(12) United States Patent
Jeong et al.

(10) Patent No.: US 10,119,753 B2
(45) Date of Patent: Nov. 6, 2018

(54) GAS SENSOR MODULE, REFRIGERATOR HAVING THE SAME AND CONTROL METHOD FOR THE REFRIGERATOR

(71) Applicant: SAMSUNG ELECTRONICS CO., LTD., Suwon-si, Gyeonggi-do (KR)

(72) Inventors: Yong Won Jeong, Seoul (KR); Young Chul Ko, Suwon-si (KR); Hyun Joo Jung, Seoul (KR); Youn Joo Song, Suwon-si (KR); Chang Hyun Lee, Suwon-si (KR); Ji Yeon Han, Suwon-si (KR)

(73) Assignee: SAMSUNG ELECTRONICS CO., LTD., Selim-si (KR)

( * ) Notice: Subject to any disclaimer, the term of this patent is extended or adjusted under 35 U.S.C. 154(b) by 274 days.

(21) Appl. No.: 14/909,356

(22) PCT Filed: Jul. 28, 2014

(86) PCT No.: PCT/KR2014/006880
§ 371 (c)(1),
(2) Date: May 3, 2016

(87) PCT Pub. No.: WO2015/016555
PCT Pub. Date: Feb. 5, 2015

(65) Prior Publication Data
US 2016/0252297 A1    Sep. 1, 2016

(30) Foreign Application Priority Data

Aug. 1, 2013 (KR) .................. 10-2013-0091426
Jul. 25, 2014 (KR) .................. 10-2014-0094563

(51) Int. Cl.
*F25D 29/00* (2006.01)
*G01N 33/00* (2006.01)
(Continued)

(52) U.S. Cl.
CPC .......... *F25D 29/006* (2013.01); *F25D 29/00* (2013.01); *G01N 21/783* (2013.01); *G01N 21/80* (2013.01);
(Continued)

(58) Field of Classification Search
CPC .... G01N 21/80; G01N 27/26; G01N 27/4167; G01N 31/221; G01N 33/0047; G01N 33/0054
See application file for complete search history.

(56) References Cited

U.S. PATENT DOCUMENTS 4,044,160 A * 8/1977 Erickson ................ A01N 31/16
                                                              252/404
4,353,867 A * 10/1982 Luzzana ............ G01N 27/3271
                                                              204/403.14
(Continued)

FOREIGN PATENT DOCUMENTS

CN    1474941    2/2004
CN    1488907    4/2004
(Continued)

OTHER PUBLICATIONS

Chinese Office Action dated Nov. 1, 2017 in Chinese Patent Application No. 201480054761.3.
(Continued)

*Primary Examiner* — Henry Crenshaw
(74) *Attorney, Agent, or Firm* — Staas & Halsey LLP

(57) ABSTRACT

A gas sensor module, a refrigerator having the same and a control method for the refrigerator. In another aspect, in a gas sensor module, ion pairs are pre-dissolved in an aqueous solution while the amount thereof and pH of an initial aqueous solution may be adjusted to adjust a sensing range and sensitivity with respect to a target gas to be sensed. In another aspect, the gas sensor module senses the amount of (Continued)

target gas includes an aqueous solution in which ion pairs of a substance having the same dissociation constant as the target gas are dissolved, and senses a pH change of the aqueous solution that occurs due to the target gas being dissolved in the aqueous solution.

19 Claims, 34 Drawing Sheets

(51) Int. Cl.
    *G01N 21/78* (2006.01)
    *G01N 21/80* (2006.01)
    *G01N 27/26* (2006.01)
    *G01N 27/416* (2006.01)
    *F25D 17/04* (2006.01)
    *G01N 27/404* (2006.01)
    *G01N 31/22* (2006.01)

(52) U.S. Cl.
    CPC ......... *G01N 27/26* (2013.01); *G01N 27/4167* (2013.01); *G01N 33/0047* (2013.01); *G01N 33/0054* (2013.01); *F25D 17/042* (2013.01); *F25D 2700/00* (2013.01); *F25D 2700/06* (2013.01); *G01N 27/4045* (2013.01); *G01N 31/221* (2013.01)

(56) References Cited

U.S. PATENT DOCUMENTS

| | | | | |
|---|---|---|---|---|
| 5,004,305 | A * | 4/1991 | Montuoro | F25D 23/04 312/350 |
| 6,436,717 | B1 * | 8/2002 | Wu | G01N 21/7703 422/82.08 |
| 2002/0072079 | A1 * | 6/2002 | Woodaman | G01N 31/229 435/7.32 |
| 2002/0166776 | A1 | 11/2002 | Fikus et al. | |
| 2008/0305013 | A1 * | 12/2008 | Eden | B01L 3/508 422/400 |
| 2009/0270709 | A1 * | 10/2009 | Copp | A61B 5/04087 600/395 |
| 2011/0284394 | A1 * | 11/2011 | Masel | G01N 27/4035 205/783 |

FOREIGN PATENT DOCUMENTS

| | | |
|---|---|---|
| CN | 102538377 | 7/2012 |
| CN | 102636433 | 3/2017 |
| EP | 1271137 | 1/2003 |
| JP | 5-196597 | 8/1993 |
| JP | 200347773 * | 2/2002 |
| JP | 2003-247773 | 9/2003 |
| KR | 10-2006-0076922 | 7/2006 |
| KR | 10-2009-0074992 | 7/2009 |
| KR | 10-2013-0011896 | 1/2013 |
| WO | 02/084279 | 10/2002 |
| WO | WO 02/084279 A2 | 10/2002 |
| WO | WO02084279 A2 * | 10/2002 |
| WO | WO 2004/025254 A2 | 3/2004 |
| WO | WO 2011/142636 | 11/2011 |

OTHER PUBLICATIONS

Extended European Search Report dated Feb. 9, 2017 in corresponding European Patent Application No. 14832397.5.
Korean Office Action dated Apr. 21, 2017 in corresponding Korean Patent Application No. 10-2014-0094563.
J. W. Ross et al., "Potentiometric Gas Sensing Electrodes", Pure and Applied Chemistry, vol. 36, Issue.4, Pergamon Press, Jan. 1973, Oxford, Great Britain, pp. 473-487.
Korean Notice of Allowance dated Aug. 4, 2017 in Korean Patent Application No. 10-2014-0094563.
International Search Report dated Nov. 27, 2014, in corresponding International Application No. PCT/KR2014/006880.
European Communication under Rule 71(3) dated Mar. 15, 2018 in European Patent Application No. 14832397.5.
Chinese Notice of Allowance dated Jun. 28, 2018 in Chinese Patent Application No. 201480054761.3.

* cited by examiner

FIG. 6A

| Molec. | CO2 | O2 | ALCOHOL | Acetic acid | H2 | N2 | ACETALDEHYDE | METHYL MERCAPTENE |
|---|---|---|---|---|---|---|---|---|
| H-Const | 0.03 | 0.001 | 100 | 5,000~10,000 | 0.0007 | 0.0006 | 10 | 0.3 |
| PH-INFLUENCE | LOW | NON-EXISTENCE | LOW | HIGH | NON-EXISTENCE | NON-EXISTENCE | LOW | LOW |
| CHARACTERISTICS | NON-POLARITY | NON-POLARITY | POLARITY | POLARITY | NON-POLARITY | NON-POLARITY | POLARITY | NON-POLARITY |

FIG. 6B

| Molec. | AMMONIA (NH3) | METHYL MERCAPTENE | ACETALDEHYDE | VOCs (pentane) |
|---|---|---|---|---|
| H-Const | 50 | 0.3 | 10 | 0.0008 |
| PH INFLUENCE | HIGH | LOW | LOW | LOW |
| CHARACTERISTICS | POLARITY | NON-POLARITY | NON-POLARITY | MEDIUM POLARITY |

GAS SENSOR MODULE, REFRIGERATOR HAVING THE SAME AND CONTROL METHOD FOR THE REFRIGERATOR

CROSS-REFERENCE TO RELATED APPLICATIONS

This application is a U.S. national stage application of International Patent Application No. PCT/KR2014/006880 filed on Jul. 28, 2014 and claims foreign priority benefit of Korean Patent Application No. 10-2013-0091426 filed Aug. 1, 2013 in the Korean Intellectual Property Office and of Korean Patent Application No. 10-2014-0094563 filed Jul. 25, 2014 in the Korean Intellectual Property Office, the content of each of the foregoing is incorporated herein by reference.

BACKGROUND

1. Technical Field

The present disclosure relates to a gas sensor module for sensing an amount of gas, an electronic product including the gas module and a control method for the electronic product.

2. Background Art

A gas sensor is a device for sensing a concentration of a particular gas, and includes a semiconductor type gas sensor, a catalytic combustion type sensor, an electrochemical sensor, etc. in accordance with a sensing principle. Out of these, the semiconductor type gas sensor uses a method of sensing an influence on a change of a resistance component as a target substance to be sensed is oxidized or reduced, and the electrochemical gas sensor uses a method of sensing an amount of ions generated due to oxidizing/reducing a gas dissolved in an electrolyte.

Since most gases except an inert gas have an oxidizing/reducing tendency, a crosstalk phenomenon in which another gas coexisting with a target gas is also sensed occurs in the semiconductor type gas sensor or the electrochemical gas sensor. Consequently, a limit exists in sensing selectivity which is capable of selectively sensing a particular gas.

In addition, whereas an olfactory organ of the human body may detect a gas causing an odor near a ppb level, a current gas sensor has lower sensitivity of sensing than the olfactory organ of the human body and thus has a difficulty in sensing a gas at or below a ppm level.

SUMMARY

The present disclosure is directed to providing a gas sensor module capable of improving selectivity and sensitivity with respect to a target gas by dissolving the target gas in an aqueous solution to sense a pH change of the aqueous solution, an electronic product having the same and a control method for the electronic product.

One aspect of the present disclosure provides a gas sensor module capable of improving selectivity and sensitivity with respect to a target gas by dissolving the target gas in an aqueous solution to sense a pH change of the aqueous solution, a refrigerator having the same and a control method for the refrigerator.

In addition, one aspect of the present disclosure provides a gas sensor module in which ion pairs are pre-dissolved in an aqueous solution while the amount thereof and pH of an initial aqueous solution may be adjusted to adjust a sensing range and sensitivity with respect to a target gas to be sensed, a refrigerator having the same and a control method for the refrigerator.

According to one aspect of the present disclosure, the gas sensor module for sensing the amount of target gas includes an aqueous solution in which ion pairs of a substance having the same dissociation constant (pKa) as the target gas are dissolved, and senses a pH change of the aqueous solution that occurs due to the target gas being dissolved in the aqueous solution.

The target gas may be a volatile organic acid or ammonia.

A resolution of the gas sensor module may vary in accordance with the concentration of the ion pairs dissolved in the aqueous solution.

The sensing range with respect to the concentration of the target gas may vary in accordance with an initial pH of the aqueous solution.

When the target gas is a volatile organic acid, the aqueous solution may have an initial pH that is higher than the dissociation constant of the target gas.

The aqueous solution may have the initial pH of 6 or higher.

When the target gas is acetic acid, 0.1 mM to 100 mM of acetate ions may be dissolved in the aqueous solution.

When the target gas is ammonia, the aqueous solution may have an initial pH that is lower than the dissociation constant of the target gas.

The aqueous solution may have the initial pH of 7 or lower.

When the target gas is ammonia, 1 µM to 10 mM of ammonium ions are dissolved in the aqueous solution.

At least one selected from a group consisting of ethylene glycol, glycerol, and polyethylene glycol may be added to the aqueous solution.

The gas sensor module may further include an electrochemical sensor to sense the pH change.

The electrochemical sensor may include a working electrode, the potential of which varies in accordance with the pH change within the aqueous solution, and a reference electrode that becomes a reference of the working electrode.

The gas sensor module may further include a housing to accommodate the aqueous solution and have an inlet into which a gas is introduced, and a porous membrane through which gas introduced through the inlet permeates.

The porous membrane may include a porous polytetrafluoroethylene membrane.

The working electrode and the reference electrode have a form of a metallic thin film and are immersed in the aqueous solution.

The gas sensor module may further include a voltmeter to sense a potential difference between the working electrode and the reference electrode.

The working electrode may be a platinum electrode, and the reference electrode may be a silver chloride (Ag/AgCl) electrode.

100 mM to 4M of chlorine ions are dissolved in the aqueous solution.

The aqueous solution is mixed with a pH indicator, the color of which varies in accordance with the pH change of the aqueous solution.

When the target gas is a carboxylic acid, the pH indicator may be at least one selected from a group including 0.001 wt % to 0.1 wt % of bromothymol blue and 0.001 wt % to 0.1 wt % of methyl red.

When the target gas is ammonia, the pH indicator may be at least one selected from a group including 0.001 wt % to 0.1 wt % of thymol blue reagent, 0.001 wt % to 0.1 wt % of cresol red, and 0.001 wt % to 0.1 wt % of phenolphthalein reagent.

The gas sensor module may further include a housing to accommodate the aqueous solution and have an inlet into which a gas is introduced, and a porous membrane through which gas introduced through the inlet permeates.

The porous membrane may include a porous polytetrafluoroethylene membrane.

The aqueous solution may exist in a liquid state or a gel state.

The housing may include fiber therein, and the aqueous solution may be absorbed into the fiber and fixed.

The housing may be formed of a material that does not have gas permeability and is transparent.

According to one aspect of the present disclosure, an electronic product includes the gas sensor module.

The electronic product may further include a signal reception unit to receive a signal output from the gas sensor module, and a control unit to determine a state of target food based on the received signal.

The control unit may prestore information on a relation between the signal output from the gas sensor module and the state of the target food, and may determine the state of the target food in accordance with the stored information.

The electronic product may further include a communication unit 540 to communicate the determined state of the target food to a refrigerator.

The electronic product may further include a display unit to display the determined state of the target food.

The electronic product may be a refrigerator, and the control unit may control a temperature of the refrigerator in accordance with the determined state of the target food.

The refrigerator may further include an input unit to receive an input of a desired state of the target food, and the control unit may control the temperature of the refrigerator based on the input desired state of the target food and the determined state of the target food.

The electronic product may further include an optical sensor to detect a color of the gas sensor module, and a control unit to determine a state of a food based on the color detected by the optical sensor.

The electronic product may further include the communication unit 540 to commmunicate the determined state of the desired food to the refrigerator.

The electronic product may further include the display unit to display the determined state of the target food.

The electronic product may be a refrigerator, and the control unit may control a temperature of the refrigerator in accordance with the determined state of the target food.

The refrigerator may further include an input unit to receive an input of a desired state of the target food, and the control unit may control the temperature of the refrigerator based on the input desired state of the target food and the determined desired state of the target food.

A control method for an electronic product that includes an aqueous solution in which ion pairs of a substance having the same dissociation constant (pKa) as a target gas are dissolved and a gas sensor module to sense a pH change of the aqueous solution that occurs due to the target gas being dissolved in the aqueous solution includes receiving a signal output from the gas sensor module, determining a concentration of the target gas based on the received signal, and determining a state of target food based on the concentration of the target gas.

The control method for the electronic product may further include displaying the determined state of the target food.

The electronic product may be a refrigerator, and the control method for the electronic product may further include controlling a temperature of the refrigerator based on the determined state of the target food.

A control method for an electronic product that includes an aqueous solution in which ion pairs of a substance having the same dissociation constant (pKa) as a target gas are dissolved and a gas sensor module to sense a pH change of the aqueous solution that occurs due to the target gas being dissolved in the aqueous solution includes detecting a color of the gas sensor module, determining a concentration of the target gas based on the detected color, and determining a state of target food based on the concentration of the target gas.

According to a gas sensor module and a home appliance having the same in accordance with one aspect of the present disclosure, a target gas is dissolved in an aqueous solution to sense a pH change of the aqueous solution, thereby improving selectivity and sensitivity with respect to a target gas to be sensed.

In addition, according to one aspect of the present disclosure, ion pairs are pre-dissolved in the aqueous solution while the amount thereof and pH of an initial electrolyte are adjusted, thereby adjusting a sensing range and sensitivity with respect to the target gas to be sensed.

According to the above-mentioned gas sensor module, electronic product having the same, and control method for the electronic product, a target gas is dissolved in an aqueous solution to sense a pH change of the aqueous solution, thereby improving selectivity and sensitivity with respect to the target gas.

BRIEF DESCRIPTION OF DRAWINGS

FIG. 6A is a table illustrating characteristics and Henry constant values for each type of gas generated during the maturity of Kimchi.

FIG. 6B is a table illustrating characteristics and Henry constant values for each type of gas generated during the refrigeration of meat.

DESCRIPTION OF EMBODIMENTS

Hereinafter, embodiments of a gas sensor module, a refrigerator having the same and a control method for the refrigerator according to one aspect of the present disclosure will be described in detail with reference to the accompanying drawings.

A gas sensor module according to an embodiment of the present disclosure may be used in various fields in which a particular gas is sensed. For example, the gas sensor module may be used in an environmental management field, a safety management field, a medical diagnosis field, a food management field, etc. To describe configurations and operations of the present disclosure in detail, a case in which the gas sensor module is used in the food management field of monitoring a state of food will be described as an example in the embodiments to be described below.

Figure 1:
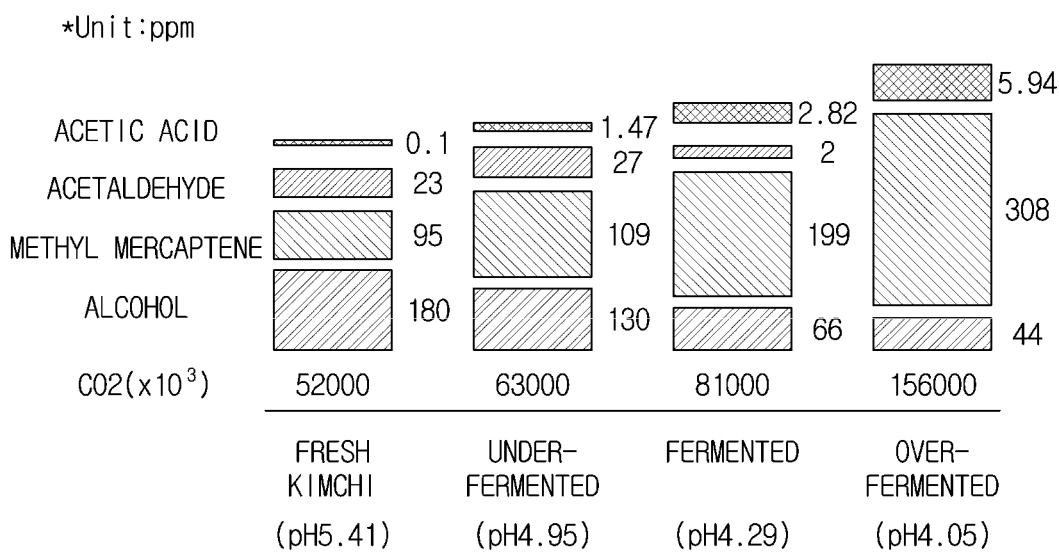
FIG. 1 is a diagram illustrating types and concentrations of gases that are generated in accordance with the degree of maturity of Kimchi.
Figure 2:
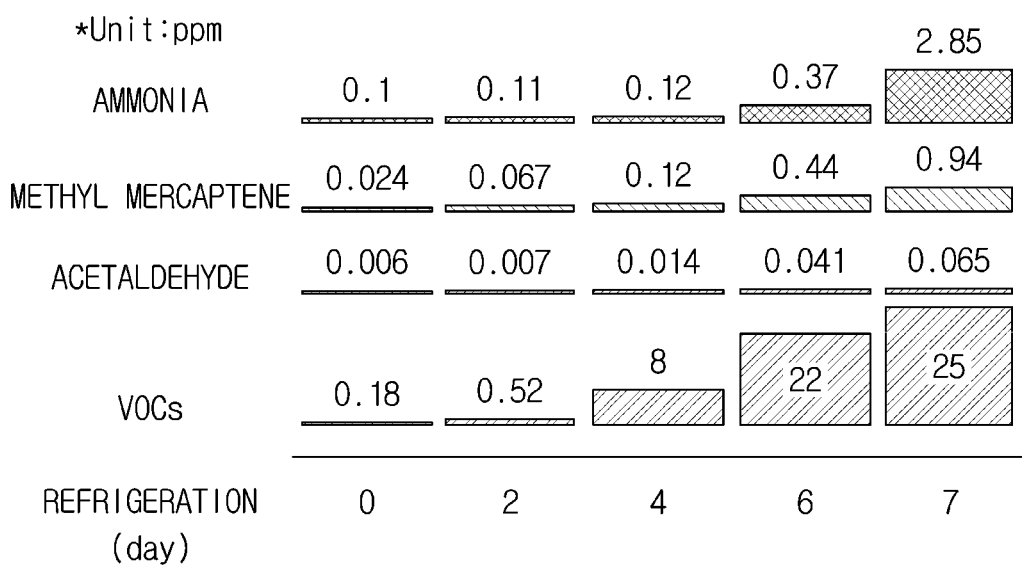
FIG. 2 is a diagram illustrating types and concentrations of gases that are generated in accordance with the degree of maturity of meat.

FIG. 1 is a diagram illustrating types and concentrations of gases that are generated in accordance with the degree of maturity of Kimchi, and FIG. 2 is a diagram illustrating types and concentrations of gases that are generated in accordance with the degree of maturity of meat.

Since various types of gases are generated during the maturity or spoilage of food, the types and amounts of the generated gases are not only affected by the degree of maturity of the food itself but also greatly affected by added spices or additional ingredients.

Among the generated gases, gas components closely related to the degree of maturity of food include a volatile organic acid, ammonia, etc. These gas components are not detected in a fresh state, and concentrations thereof increase proportionally to the degree of maturity as the food matures.

Referring to FIG. 1, when kimchi, which is fermented food, matures, gases such as acetic acid, acetaldehyde, methylmer captene, and alcohol are generated. Here, although mainly generated gases are acetaldehyde, methylmer captene, and alcohol, these gases are ingredient-dependent gases that are generated in salted seafood, spices, etc. and do not have an absolute correlation with the degree of fermentation or maturity of kimchi.

A gas directly involved with the fermentation is a volatile organic acid that is generated as a byproduct of a microorganism, and acetic acid is marked as the exemplary volatile organic acid in FIG. 1. As illustrated in FIG. 1, acetic acid is almost not generated at an initial stage of the fermentation, and gradually increases as fermentation progresses. However, the concentration thereof is only about a few ppm that is substantially lower than those of other gases.

Consequently, in a case of fermented food such as kimchi, the degree of maturity thereof may be determined only when the volatile organic acid having a low concentration of 1 ppm or lower is detected among other gases having the maximum concentration of hundreds of ppm.

In a case of a human olfactory organ, the volatile organic acid may be mostly distinguished from other gases even under a hundreds-to-one selectivity condition despite differences for each individual. However, most currently-commercialized gas sensors have a difficulty in selectively sensing only the volatile organic acid of about a few ppm among other gas components of hundreds of ppm.

Even in a case of general food that is not fermented food, the degree of maturity or the degree of spoilage may be determined from generated gas components. In a case of meat, when stored for a long period at a low temperature, amino acids increase as proteins are degraded by a microorganism. Since the maturity of meat may be basically viewed as a gradual process of spoilage, gases such as ammonia, methylmer captene, acetaldehyde, and volatile organic compounds (VOCs) are generated in a metabolic process of an amino acid by bacteria propagating within proteins as illustrated in FIG. 2.

However, since variations occur in accordance with a type or a part of meat in the gases of methylmer captene, acetaldehyde, and VOC within the same types of gases, a gas that may be an index of the degree of maturity or the degree of spoilage of meat as a single gas is ammonia. As illustrated in FIG. 2, since a generated amount of ammonia in accordance with the degree of maturity of meat is not great, the degree of maturity of meat may be accurately determined only when having a resolution less than 1 ppm. The resolution and sensitivity are factors representing the lowest extent of concentration that may be sensed by a sensor.

According to the above described, to determine the degree of fermentation or the degree of maturity of food, high selectivity and sensitivity (resolution of sub ppm) are required to selectively detect a particular gas of a ppm level among another gas component of hundreds of ppm.

According to one aspect of the disclosed disclosure, since the gas sensor module employs a reaction principle that is similar to an olfactory system of humans and is able to realize high selectivity and sensitivity (resolution of sub ppm), a structure and an operational principle of the gas sensor module in accordance with one aspect of the present disclosure will be described in detail below.

Figure 3:
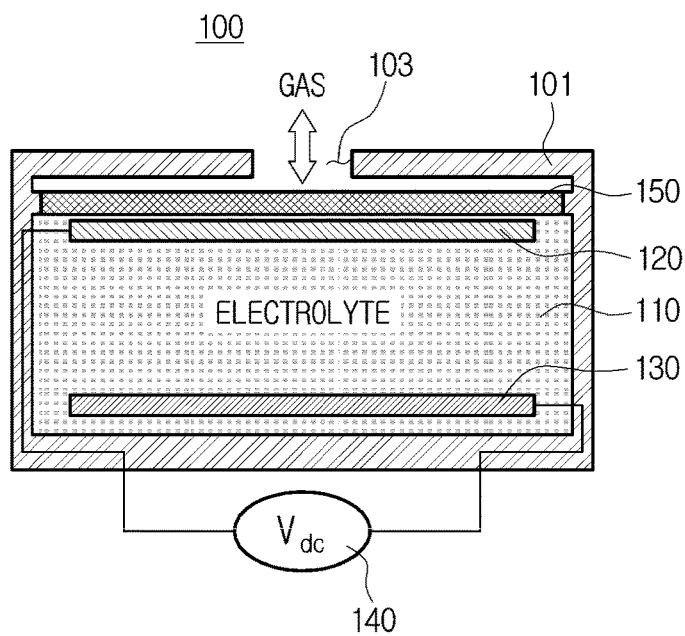
FIG. 3 is a cross-sectional view illustrating a structure of a gas sensor module according to an embodiment of the present disclosure.

FIG. 3 is a cross-sectional view illustrating a structure of a gas sensor module according to an embodiment of the present disclosure.

Referring to FIG. 3, according to an embodiment of the present disclosure, a gas sensor module 100 includes an aqueous solution 110 to fill an inner portion of a housing 101, metal electrodes 120 and 130 to sense a pH change that occurs when a target gas is dissolved in the aqueous solution 110, and a voltmeter 140 to sense a potential difference between the metal electrodes 120 and 130. The sensed potential difference is proportional to a concentration of the target gas to be sensed.

The target gas to be sensed is introduced through an inlet 103 formed at an upper portion of the housing 101, and a porous membrane 150 is disposed at a lower portion of the inlet 103 to enable an external gas component to be fully introduced while maximally suppressing the evaporation of an electrolyte.

Since the porous membrane 150 is formed of a material having gas permeability, most gas-permeable resins including a fluorinated ethylene propylene (FEP) film, which is a porous polytetrafluoroethylene (PTFE) film, may be used.

Hereinafter, a specific operation and a principle thereof of the gas sensor module 100 will be described with reference to the structure of FIG. 3.

As mentioned above, since the gas sensor module 100 employs the principle of the human olfactory system, the aqueous solution 110 filling the inner portion of the housing 101 serves a function of a mucous layer of a human epithelial tissue that collects odor molecules in the air. The aqueous solution 110 may selectively collect gases that dissolve in water.

In the above described, it was described that a volatile organic acid gas and ammonia gas may be important indexes in determining the degree of fermentation or the degree of maturity of food. Consequently, the gas sensor module 100 may have the volatile organic acid gas or the ammonia gas as a target gas. That is, the gas sensor module 100 may be configured to sense the concentration of the volatile organic acid gas or the ammonia gas.

The volatile organic acid gas and the ammonia gas are polarizable substances that dissolve only in water, and the aqueous solution 110 may selectively collect water-soluble molecules such as the volatile organic acid or the ammonia rather than fat-soluble molecules such as methylmer captene or VOCs among various gas components existing in an external environment of the gas sensor module 100. That is, the aqueous solution 110 plays a role of filtering most methylmer captene and VOCs generated in food to improve selectivity with respect to the target gas of the gas sensor module 100.

The volatile organic acid and ammonia both cause a concentration change of hydrogen ions by being dissociated when dissolved in the aqueous solution. In the case of a carboxylic acid (R—COOH), which is a representative volatile organic acid, hydrogen ions are generated when R—COOH is dissolved in the aqueous solution, thus decreasing the pH of the aqueous solution. In the case of ammonia (NH3), the number of hydrogen ions of the aqueous solution decrease when NH3 is dissolved in the aqueous solution, thus increasing the pH.

Since the gas sensor module 100 senses the pH change by an electrochemical method, when the volatile organic acid or ammonia is dissolved in the aqueous solution 110 and causes the pH change of the aqueous solution 110, a potential difference between the two metal electrodes 120 and 130 is generated in accordance with the pH change, and the voltmeter 140 senses the potential difference. The sensed potential difference is proportional to the concentration of the volatile organic acid or ammonia dissolved in the aqueous solution 110.

Hereinafter, a design of the aqueous solution 110 that enables the gas sensor module 100 to have superior selectivity and resolution by having acetic acid, which is a representative volatile organic acid, as the target gas, will be described in detail.

When the acetic acid is dissolved in the aqueous solution, the acetic acid is separated into acetate ions and hydrogen ions in accordance with Chemical Formula 1 below. This is referred to as dissociation.

$$CH_3COOH \leftrightarrow CH_3COO^- + H^+ \quad \text{[Chemical Formula 1]}$$

An extent to which the acetic acid is dissociated in the aqueous solution may be represented as an ionization constant or a dissociation constant in accordance with Equation 1 below.

$$K_a = [CH_3COO^-][H^+]/[CH_3COOH] = 1.8 \times 10^{-5} \quad \text{[Equation 1]}$$

That is, the ionization constant ($K_a$) is $1.8 \times 10^{-5}$, and since the value is too small, it may also be represented as pKa 4.7.

After the acetic acid is dissociated, original characteristics of the acetic acid are lost, and pH decreases as the dissociation continues.

Figure 4:
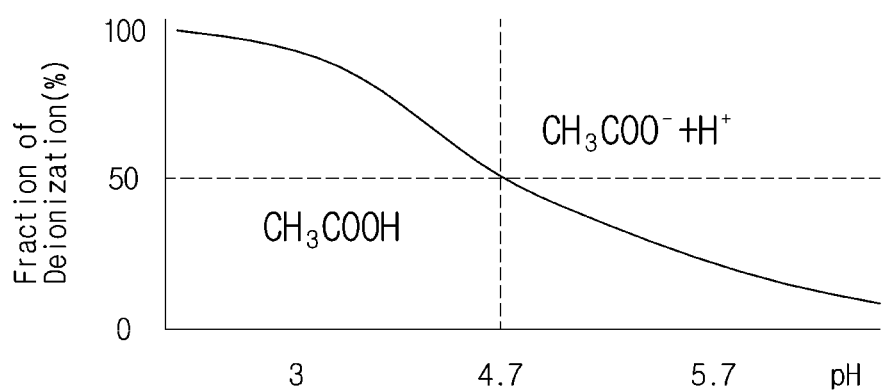
FIG. 4 is a graph illustrating a curve of the degree of dissociation of acetic acid in accordance with the pH change of an aqueous solution.

FIG. 4 is a graph illustrating a curve of the degree of dissociation of acetic acid in accordance with the pH change of an aqueous solution. Since the y-axis of the graph of FIG. 4 is the fraction of deionization, a greater y-coordinate value represents a lower degree of dissociation and a smaller y-coordinate value represents a higher degree of dissociation.

Referring to FIG. 4, when the pH of the aqueous solution in which the acetic acid is dissolved is 4.7, which is the same as the pKa of the acetic acid, since the degree of dissociation of the acetic acid is 50%, half of the acetic acid is dissociated and thus loses its characteristics, whereas the other half thereof is not dissociated and thus maintains its characteristics.

When the pH of the aqueous solution becomes lower than 4.7, the degree of dissociation of the acetic acid sharply decreases, and most of the acetic acid remains as it is without being dissociated.

Conversely, when the pH of the aqueous solution becomes higher than 4.7, the degree of dissociation of the acetic acid increases, and the acetic acid is continuously dissociated. When the acetic acid is continuously dissociated in the aqueous solution, the number of hydrogen ions in the aqueous solution increases, and thus the pH is lowered. When the pH is lowered, the acetic acid of a predetermined concentration or more exists without being dissociated, and the acetic acid, which is a volatile organic acid, is prone to evaporate again when it exists in the aqueous solution without being dissociated.

Consequently, when the aqueous solution is exposed to an environment where the acetic acid gas of a predetermined concentration exists, as the pH decreases due to the continuous dissociation of the acetic acid dissolved in the aqueous solution and the undissociated acetic acid in the aqueous solution evaporates, gases introduced from the outside and gases being evaporated reach a dynamic equilibrium state. That is, the pH of the aqueous solution reaches an equilibrium state where it is unchanged.

In addition, when the acetic acid gas does not exist in the external environment, the acetic acid in the aqueous solution continuously evaporates, causing the pH to increase again. Using this principle, the gas sensor module 100 may secure reversibility, and control a sensing resolution and a sensing range.

Since the sensing range and the sensing resolution required for the gas sensor module 100 is different in accordance with its purpose, a composition ratio of the aqueous solution 110 may be adjusted to realize a desired sensing range and sensing resolution.

Equation 2 below shows the Henderson-Hasselbalch equation with respect to the acetic acid and acetate ions obtained from Equation 1. Here, the acetic acid and the acetate ions are in a relation of a conjugate acid and a conjugate base.

$$pH = pK_a + \log [CHCOO^-]/[CH_3COOH] \quad \text{[Equation 2]}$$

According to Equation 2, the pH of the aqueous solution is determined by a ratio of dissolved acetate ions and acetic acid. Consequently, when the acetate ions are pre-dissolved in an initial aqueous solution, a pH reactivity with respect to the acetic acid varies in accordance with the amount of pre-dissolved acetate ions.

Consequently, the amount of acetate ions dissolved in the initial aqueous solution 110 and an initial pH value of the aqueous solution 110 may be adjusted to control the reactivity and the sensing range with respect to the target gas to be sensed.

Figure 5A:
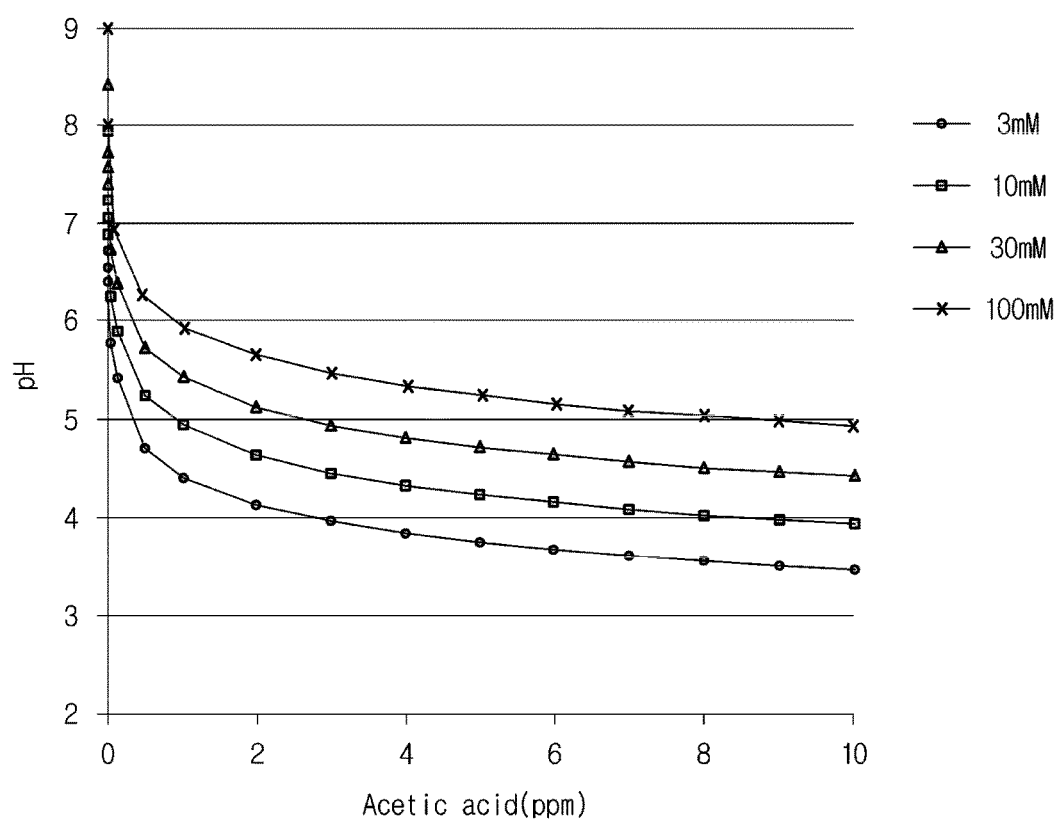
FIG. 5A is a graph illustrating a pH change of an aqueous solution in accordance with an acetic acid concentration of an external environment for respective amounts of acetate ions pre-dissolved in the aqueous solution.
Figure 5B:
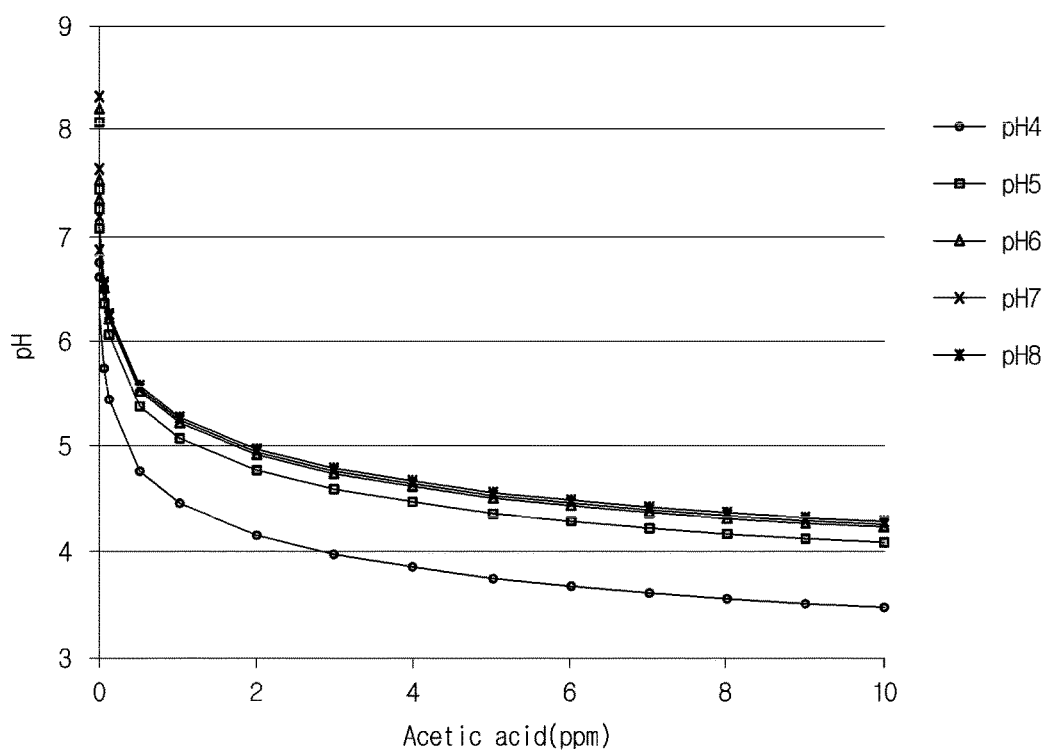
FIG. 5B is a graph illustrating a pH change of an aqueous solution in accordance with an acetic acid concentration of an external environment for respective initial pHs of the aqueous solution.

FIG. 5A is a graph illustrating a pH change of an aqueous solution in accordance with an acetic acid concentration of an external environment for respective amounts of acetate ions pre-dissolved in the aqueous solution, and FIG. 5B is a graph illustrating a pH change of an aqueous solution in accordance with an acetic acid concentration of an external environment for respective initial pHs of the aqueous solution.

The graph of FIG. 5A shows a pH change of an aqueous solution with an initial pH of 8 in accordance with a concentration of acetic acid gas calculated for cases where an initial concentration of acetate ions is 3 mM, 10 mM, 30 mM, and 100 mM. The initial concentration of acetate ions refer to a concentration of acetate ions pre-dissolved in the aqueous solution.

Referring to FIG. 5A, the pH change of the aqueous solution in accordance with the change in acetic acid gas concentration is the greatest when the initial concentration of acetate ions is 3 mM, and particularly, the pH change is great even with respect to the acetic acid gas of 1 ppm or lower. From this, it can be recognized that the reactivity with respect to the acetic acid gas is superior as the initial concentration of acetate ions is small.

Meanwhile, when considering that it is actually difficult for the pH of the aqueous solution to be dropped to 3 or lower no matter how high the concentration of the acetic acid, which is a weak acid, a limit exists in sensing a concentration of the acetic acid gas of 10 ppm or higher when the initial concentration of acetate ions is 3 mM.

Conversely, when the initial concentration of acetate ions is 100 mM, the pH change with respect to the acetic acid gas of 1 ppm or lower is not great compared to the case in which the initial concentration of acetate ions is 3 mM. Instead, since the pH remains at about 5 even when the concentration of acetic acid of the external environment is 10 ppm, it is predicted that the pH change may be sensed even in an environment of high-concentration acetic acid gas of 10 ppm or higher.

FIG. 5B shows a pH change in accordance with the concentration of acetic acid gas calculated while fixing the initial concentration of acetate ions of the aqueous solution to 30 mM and changing the initial pH of the aqueous solution.

Referring to FIG. 5B, it may be recognized that a sensing range of the acetic acid gas is 3 ppm or higher when the initial pH of the aqueous solution is 4 since the pH of the aqueous solution drops to 4 or lower only when the acetic acid gas of 3 ppm or higher exists, and it may be recognized that the sensing range of the acetic acid gas is 3 ppm or higher when the initial pH of the aqueous solution is 5 since the pH of the aqueous solution drops to 5 or lower only when the acetic acid gas of 1 ppm or higher exists. Waveforms are similar in cases where the initial pH of the aqueous solution is 6, 7, and 8.

Based on the description related to FIGS. 5A and 5B, the composition of the aqueous solution 110 may be determined. That is, since the initial concentration of acetate ions and the initial pH of the aqueous solution may be determined in accordance with a desired sensing resolution and sensing range, an optimal sensing resolution and sensing range may be realized by determining the composition of the aqueous solution 110 in consideration of a purpose or a service environment of the gas sensor module 100.

Although a target gas has been described as the acetic acid in the above embodiment, the same description may be applied with respect to a volatile organic acid that is not acetic acid. Consequently, even when the target gas is a volatile organic acid other than the acetic acid, a desired sensing range and sensing resolution may be realized by properly adjusting the initial pH of the aqueous solution 110 and a concentration of a conjugate base of a pre-dissolved volatile organic acid.

When the target gas is a carboxylic acid, 0.1 mM to 100 mM of acetate ions may be pre-dissolved in the aqueous solution 110. Here, sodium chloride (NaCl) may be used, but embodiments are not limited thereto, and most compounds including acetate ions may be used.

Although the initial pH of the aqueous solution 110 may vary in accordance with a desired sensing range, it should have a greater value than the pKa of the target gas. For example, when the target gas is a volatile organic acid, the initial pH of the aqueous solution 110 may be 6 or higher to sense the volatile organic acid in a wide concentration range.

In addition, even when the target gas is ammonia, a desired sensing range and sensing resolution may be realized by properly adjusting the initial pH of the aqueous solution 110 and a concentration of a conjugate acid (ammonium ions, $NH_4^+$) pre-dissolved in the aqueous solution 110.

For example, 1 μM to 10 mM of ammonium ions may be pre-dissolved in the aqueous solution 110. Here, ammonium hydroxide or ammonium chloride may be used, but embodiments are not limited thereto, and most compounds including ammonium ions may be used.

Ammonia is an alkaline gas with a pKa of 9.3, and the initial pH of the aqueous solution 110 should have a smaller value than the pKa of ammonia when the target gas is ammonia. For example, an initial pH condition with a pH of 7 or lower may be used.

Furthermore, to suppress evaporation of the aqueous solution 110 and lower a freezing point, ethylene glycol, glycerol, polyethylene glycol, etc. may be added to the aqueous solution 110.

Meanwhile, a conjugate acid or a conjugate base pre-dissolved in the aqueous solution 110 does not always have to be a conjugate acid or a conjugate base of the target gas. In accordance with the Henderson-Hasselbalch equation [Equation 2] above, pre-dissolving ion pairs of a substance having the same pKa as the target gas in the aqueous solution 110 is also possible. For example, when the target gas is a volatile organic acid, a conjugate base of a substance having the same pKa as the corresponding volatile organic acid may be pre-dissolved, and when the target gas is ammonia, a conjugate acid of a substance having the same pKa as ammonia may be pre-dissolved.

FIG. 6A is a table illustrating characteristics and Henry constant values for each type of gas generated during the maturity of kimchi, and FIG. 6B is a table illustrating characteristics and Henry constant values for each type of gas generated during the refrigeration of meat.

An extent to which gaseous molecules may dissolve in water is different for each type thereof. The Henry constant may be an index showing an extent to which gaseous molecules may be dissolved in a liquid state. A greater Henry constant represents a greater water-soluble property, and a smaller Henry constant represents a greater non water-soluble property.

Referring to FIG. 6A, polar gases among gases generated during the fermentation of kimchi are alcohol, acetaldehyde, and acetic acid, and the remaining carbon dioxide ($CO_2$), oxygen ($O_2$), alcohol, hydrogen ($H_2$), and nitrogen ($N_2$) are non-polar. The $CO_2$, $O_2$, alcohol, $H_2$, and $N_2$ do not dissolve well in the aqueous solution 110.

A gas with the greatest Henry constant is acetic acid, which is a volatile organic acid. The Henry constant thereof ranges from 5000 to 10000, and is hundreds to millions of times greater compared to the remaining gases. This signifies that the acetic acid dissolves in water hundreds to millions of times better than the other gases.

Since the Henry constant of the acetic acid is much greater not only when compared to $CO_2$, $O_2$, $H_2$, $N_2$, and methylmer captene but also when compared to alcohol or acetaldehyde, it may be recognized that the gas sensor module 100 including the aqueous solution 110 may collect the acetic acid with very high selectivity among various kimchi fermentation gases.

In addition, the acetic acid also has the greatest influence on the pH of the aqueous solution among the gases generated during the fermentation of kimchi. Consequently, the gas sensor module 100 may sense the concentration of the acetic acid with a superior resolution, and since influences of alcohol, acetaldehyde, and methylmer captene on the pH of the aqueous solution are insignificant even if infinitesimal amounts of the alcohol, acetaldehyde, and methylmer captene may dissolve in the aqueous solution, the selectivity of the gas sensor module 100 may be improved secondarily.

Referring to FIG. 6B, since a gas with the highest Henry constant among gases generated in refrigerated meat is ammonia, the gas sensor module 100 may collect ammonia with high selectivity, and since the influence on the pH is also the greatest, the gas sensor module 100 may sense the concentration of ammonia with the most superior resolution.

Until now, principles by which the gas sensor module 100 collects a volatile organic acid or ammonia, which is a target gas to be sensed, and a change in the pH of the aqueous solution 110 occurs have been described. Hereinafter, a method of sensing a pH change which has occurred in the aqueous solution 110 by the gas sensor module 100 will be described in detail with reference to FIG. 3 again.

Referring again to FIG. 3, the gas sensor module 100 senses a pH change in the aqueous solution 110 using the working electrode 120 that is sensitive to a concentration of hydrogen ions and the reference electrode 130 that does not react to the concentration of hydrogen ions. To increase the reactivity, the working electrode 120 and the reference electrode 130 may be realized in a form of a metallic thin film.

Since a platinum-based electrode may be used for the working electrode 120, most precious metal oxides such as iridium oxide, which is a hydrogen-sensitive metallic thin film, may be used. To secure reproducibility of electrode potentials and maximally increase a surface reaction, a nanoporous platinum electrode may be used, and platinum particles may be mixed with carbon powder and used.

Ag/AgCl may be used as the reference electrode 130, and a pseudo-reference such as a gold electrode may also be used in some cases. An Ag/AgCl electrode may be manufactured in a thin film form by being processed in a paste form showing viscosity.

When a predetermined concentration of Cl ions is present around AgCl, a surface reaction of Ag/AgCl is not affected by other ions or components and is dependent only on the concentration of Cl ions. Consequently, to use Ag/AgCl as the reference electrode 130, a predetermined Cl ion condition should be satisfied in the aqueous solution 110. For this, 100 mM to 4M of potassium chloride (KCl) or NaCl may be added, or most compounds other than the above including Cl ions may be added.

The volatile organic acid or ammonia introduced through the porous membrane 150 is dissociated in the aqueous solution 110 and causes a pH change. A potential of the working electrode 120 varies in accordance with the concentration of hydrogen ions and since the Cl ions in the aqueous solution 110 have a predetermined concentration, the reference electrode 130 has a predetermined potential regardless of the concentration of hydrogen ions.

Since the voltmeter 140 senses the potential difference between the working electrode 120 and the reference electrode 130 and the sensed potential difference is proportional to the concentration of the target gas to be sensed, it is possible to estimate the concentration of the target gas from the sensed potential difference.

Figure 7:
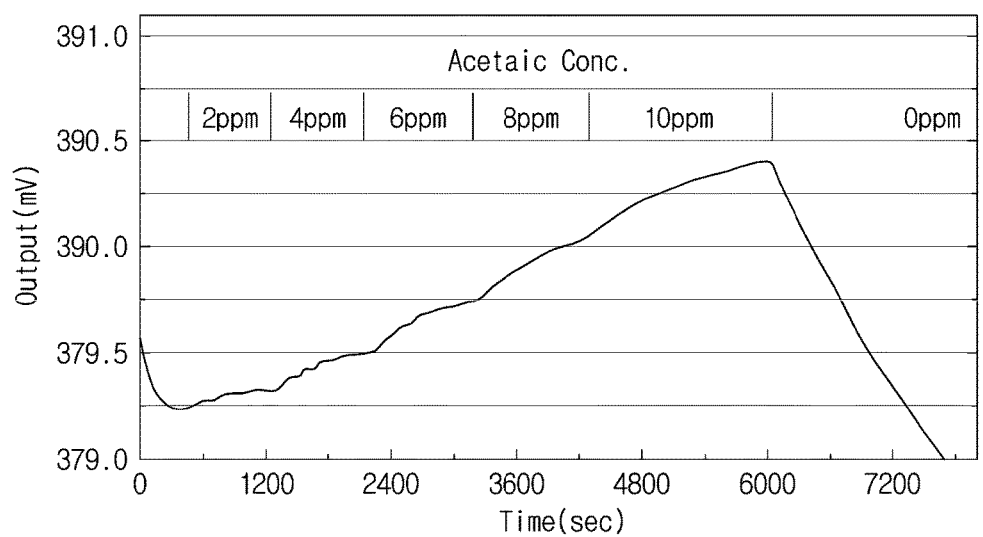
FIG. 7 is a graph illustrating an output of a gas sensor module in accordance with separate ppm levels of acetic acid concentration.

FIG. 7 is a graph illustrating an output of a gas sensor module in accordance with several concentration conditions of acetic acid.

As mentioned above, the sensing range and the resolution may be determined in accordance with the initial pH of the aqueous solution 110 and the initial concentration of acetate ions. In an experiment of FIG. 7, 30 mM of sodium acetate and 1M of sodium chloride are dissolved in the aqueous solution 110. Since these substances are 100% dissociated regardless of the pH of the solution, 30 mM of acetate ions (CH3COO—) and 1M of chloride ions (Cl—) are dissolved in the aqueous solution 110 and participate in an electrochemical reaction. Additionally, 1M of sodium ions (Na+) may be added, but the sodium ions do not participate in the electrochemical reaction.

The graph of FIG. 7 shows an output of the gas sensor module 100 sensed up to 10 ppm while increasing the concentration of external acetic acid gas by 2 ppm from 2 ppm in the above condition. Also, the concentration of external acetic acid gas was dropped to 0 ppm after sensing with respect to 10 ppm was completed, and an occurrence of a reversible reaction was confirmed.

Figure 8:
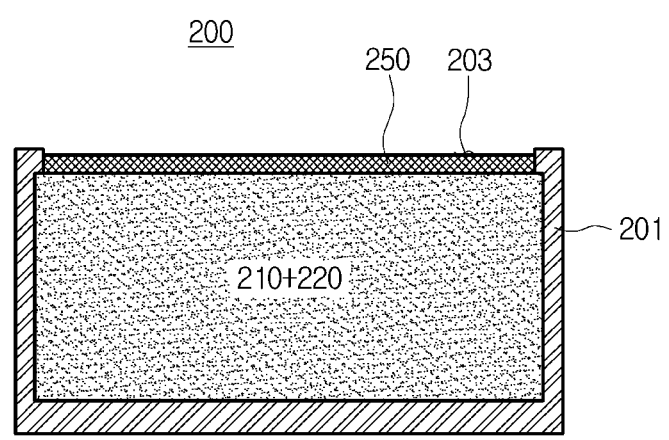
FIG. 8 is a cross-sectional view illustrating a structure of a gas sensor module according to another embodiment of the present disclosure.

FIG. 8 is a cross-sectional view illustrating a structure of a gas sensor module according to another embodiment of the present disclosure.

Referring to FIG. 8, since a gas sensor module 200 according to another embodiment of the present disclosure also has an inner portion of a housing 201 filled with an aqueous solution 210, the pH of which varies in accordance with introduction of a target gas to be sensed, description on the aqueous solution 210 is the same as the description on the aqueous solution 110 of the gas sensor module 100 according to the above-mentioned embodiment.

That is, the gas sensor module 200 is the same as the gas sensor module 100 up to the structure causing a pH change in the aqueous solution 110 by collecting a target gas to be sensed. An inlet 203 into which gas is introduced is also formed at the housing 201 of the gas sensor module 200, and a porous membrane 250 having gas permeability is provided at the inlet 203, thereby blocking evaporation of the aqueous solution 210 and enabling a gas to be fully introduced.

Since the porous membrane 250 is formed of a material having gas permeability, most gas-permeable resins including an FEP film, which is a porous PTFE film, may be used. The housing 201 is formed of a material having non-permeability of gas, and glass or various types of resins may be used.

A difference between the gas sensor module 200 according to this embodiment and the gas sensor module 100 according to the above-mentioned embodiment exists in a method of sensing a pH change.

According to this embodiment, an indicator, a color of which changes in accordance with a pH, i.e. a pH indicator 220, is added to the aqueous solution 210. Consequently, a solution filling the inner portion of the housing 201 of the gas sensor module 200 is a mixture solution of the aqueous solution 210 and the pH indicator 220. The pH indicator has a characteristic of a color being changed in accordance with the degree of reaction with hydrogen ions in the solution.

As one experimental example, 3 mM of a pH 7.6 sodium acetate buffer including bromothymol blue and methyl red as pH indicators was exposed to acetic acid. As a result of injecting 1 cc of acetic acid gas at a time, it was confirmed that the color of the solution changed to blue, yellow, and red as the amount of the injected acetic acid gas increased.

This is a combination of a result of being changed to yellow when pH becomes 6.0 from bromothymol blue showing blue when pH is 7.6, and a result of being changed to red when pH becomes 4.8 from methyl red showing yellow when pH is 6.0.

Consequently, the aqueous solution 210 may be mixed with an appropriate pH indicator 220 in accordance with a type of a target gas to be sensed and may fill the inner portion of the housing 201. Here, the mixture solution of the aqueous solution 210 and the pH indicator 220 may exist in a liquid state or a gel state, and may also be absorbed into fiber provided inside the housing 201 and fixed.

For example, when the target gas to be sensed is a carboxylic acid, 0.001 wt % to 0.1 wt % of bromothymol blue or 0.001 wt % to 0.1 wt % of methyl red indicator may be used solely or in combinations thereof.

Specifically, when the target gas to be sensed is acetic acid gas with a pKa of 4.7, 0.02 wt % of bromothymol blue and 0.005 wt % of methyl red may be reacted with 10 wt % of ethanol in accordance with the above experimental example, then dissolved in the aqueous solution 210. The ethanol is used to dissolve the pH indicator.

Otherwise, when the target gas to be sensed is ammonia, 0.001 wt % to 0.1 wt % of thymol blue, phenolphthalein, and the like, may be used, and when sensing a low concentration of ammonia, cresol red, bromothymol blue, and the like, of the same concentration level may be used solely or in combinations thereof.

Specifically, when the target gas is ammonia with a pKa of 9.3, since a pH indicator for a range including pH 9.3 is used, thymol blue in which a color change occurs between pH 8.0 and pH 9.6 may be used. Since a color change should occur even with a small pH change in order to sense small concentration of ammonia (ppm or lower), cresol red in which a color change occurs between pH 7.0 and pH 8.8 or bromothymol blue in which a color change occurs between pH 6.0 and pH 7.6 may be used.

When the appropriate pH indicator 220 is mixed with the aqueous solution 210 in accordance with the target gas and the inner portion of the housing 201 is filled therewith, the target gas existing in the external environment is introduced into the housing 201 and causes a pH change of the aqueous solution 210, and the color of the pH indicator 220 changes in accordance with the pH change. When the housing 201 is formed of a transparent material, a user may observe the color change from the outside and recognize the concentration of the target gas.

Hereinafter, an embodiment of an electronic product according to one aspect of the present disclosure will be described. The electronic product according to one aspect of the present disclosure is an electronic product to which gas sensing technology is applied, and uses the gas sensor modules 100 and 200 in accordance with the above-mentioned embodiments to sense the concentration of the target gas.

Although various types of electronic products may be applicable in an embodiment of the present disclosure, a refrigerator that determines states such as the degree of maturity or the degree of spoilage of food based on sensing of the target gas will be described as a representative example in the embodiment described with reference to FIGS. 9 to 14B, and a gas sensor assembly attached to a storage container of a refrigerator to communicate states such as the determined degree of maturity or degree of spoilage of food to the refrigerator will be described as a representative example in the embodiment described with reference to FIGS. 15 to 18B.

Figure 9:
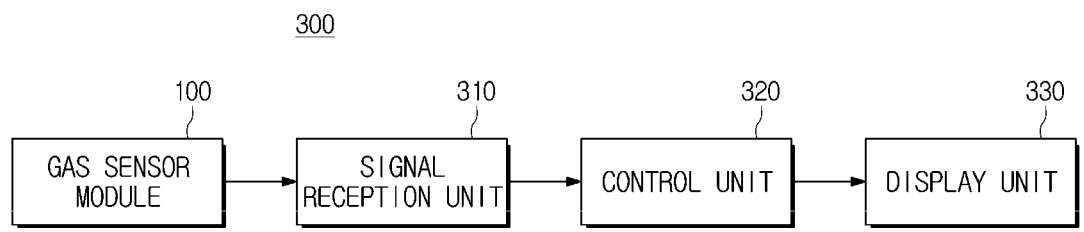
FIG. 9 is a control block diagram of an electronic product according to an embodiment of the present disclosure.
Figure 10A:
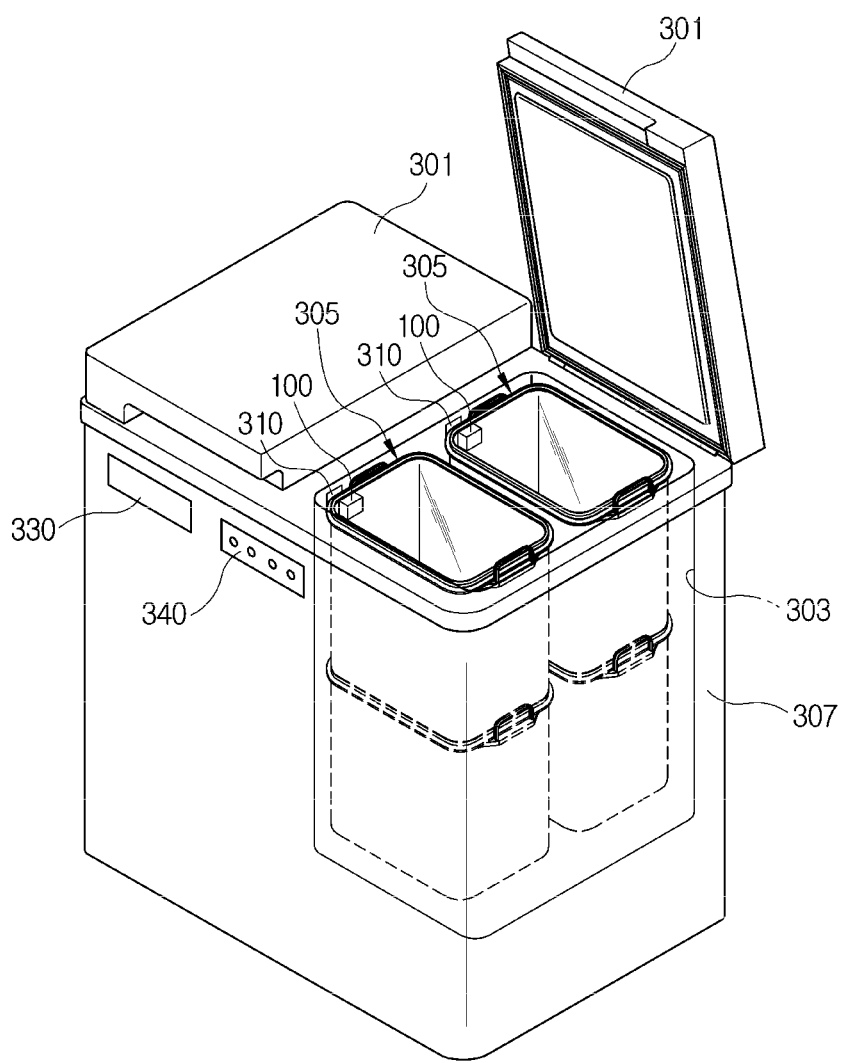
FIGS. 10A and 10B are exterior views of an electronic product according to an embodiment of the present disclosure.
Figure 10B:
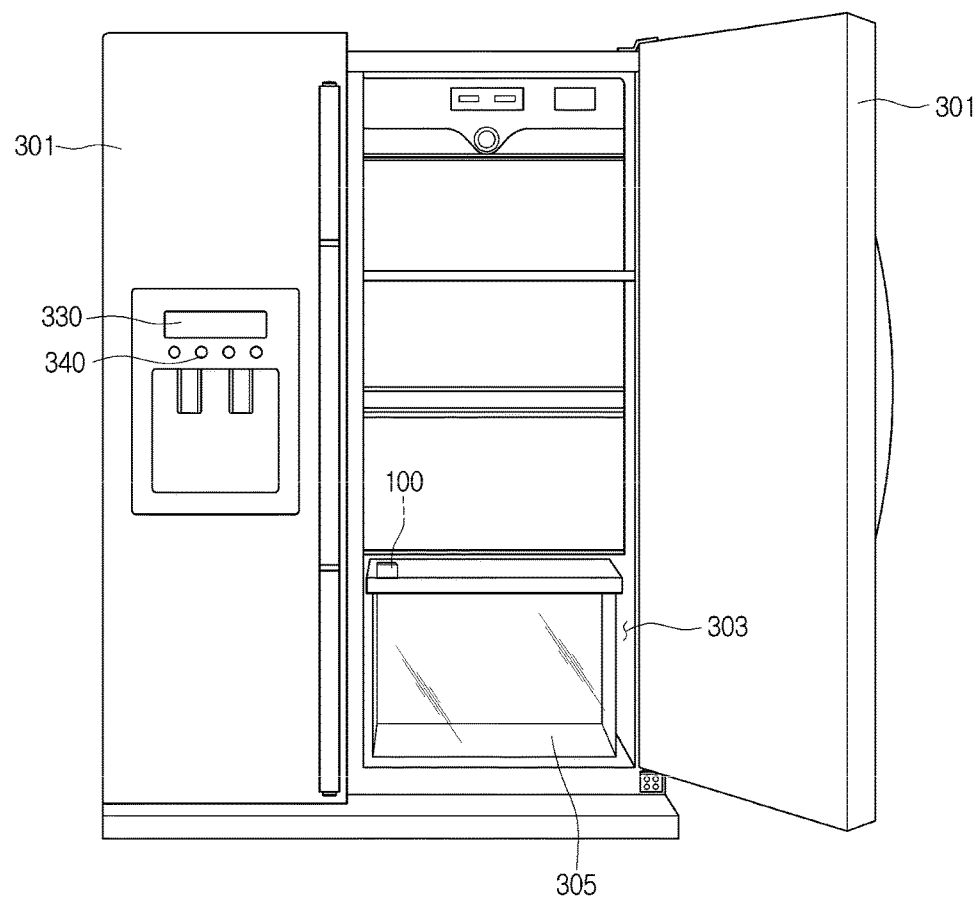

FIG. 9 is a control block diagram of an electronic product according to an embodiment of the present disclosure, and FIGS. 10A and 10B are exterior views of an electronic product according to an embodiment of the present disclosure.

According to an embodiment of the present disclosure, a refrigerator 300 includes the gas sensor module 100 in accordance with the above-mentioned embodiment, a signal reception unit 310 to receive a signal output from the gas sensor module 100, a control unit 320 to determine a state of food based on the received signal, and a display unit 330 to display the determined result.

The refrigerator 300 applied to this embodiment may be a kimchi refrigerator or a general refrigerator in accordance with its purpose. Also, since the refrigerator 300 may be classified into a stand type and a cover type in accordance with a structure or form thereof, both of the stand type and cover type may be kimchi refrigerators or general refrigerators. Since the type or purpose of the refrigerator 300 according to an embodiment of the present disclosure is not limited, any refrigerator may be the refrigerator 300 in accordance with this embodiment. The refrigerator may have a door 301.

Hereinafter, a specific configuration of the refrigerator 300 will be described with reference to FIGS. 10A and 10B.

A storage compartment 303 capable of storing food is provided in a main body 307 of the refrigerator 300, and a storage container 305 separable from the refrigerator 300 may be disposed in the storage compartment 303. The gas sensor module 100 may be mounted inside the storage container 305 to sense the concentration of the target gas among gases generated from food stored in the storage container 305.

The refrigerator 300 does not always have to include the storage container 305, and the gas sensor module 100 also does not always have to be mounted in the storage container 305. The gas sensor module 100 only has to be mounted inside the refrigerator 300, but since the gas sensor module 100 is not affected by other gases except a gas generated in food, a state of which is to be determined, when mounted in a sealed storage container 305, the gas sensor module 100 may more accurately sense the concentration of the target gas when mounted in the storage container 305.

The signal reception unit 310 is provided at an inner wall of the storage compartment 303 to receive an output signal of the gas sensor module 100. Specifically, when the gas sensor module 100 is mounted inside the storage container 305 as illustrated in FIGS. 10A and 10B, an output terminal of the gas sensor module 100 may be exposed outside the storage container 305 and may come in contact or may be connected to the signal reception unit 310 provided at the inner wall of the storage compartment 303 in order to receive the output signal of the gas sensor module 100 by wire. Conversely, when communicating wirelessly, a communication unit 540 of the gas sensor module 100 and the signal reception unit 310 may be paired through a wireless session, and the gas sensor module 100 may transmit the output signal to the signal reception unit 310 such that the signal reception unit 310 may wirelessly receive the output signal.

A communication method of the signal reception unit 310 may be the same or different from the communication method of the communication unit 540 of FIGS. 15A and 15B below.

When the refrigerator 300 has a stand type structure, since the signal reception unit 310 may be provided at a rear surface of an inner wall of the main body 307, the storage container 305 may be disposed at the storage compartment 303 such that a portion thereof on which the gas sensor module 100 is mounted faces the rear surface of the main body 307 as illustrated in FIG. 10B.

Consequently, the gas sensor module 100 outputs a signal in accordance with the concentration of the target gas generated in the stored food, and the signal reception unit 310 receives the output signal of the gas sensor module 100 and transmits the signal to the control unit 320.

The gas sensor module 100 and the signal reception unit 310 may be mounted at positions corresponding to each other by considering a position relation between each other.

The control unit 320 determines the state of food based on the output signal of the gas sensor module 100. As mentioned above, since the amount of generated target gas varies in accordance with the degree of maturity or the degree of spoilage of food, the control unit 320 may store the degree of maturity or the degree of spoilage of food in accordance with the amount of target gas in a form of a database, and determine the degree of maturity or the degree of spoilage of food corresponding to the output signal of the gas sensor module 100.

Since an output value of the gas sensor module 100 may be different in accordance with a type and size of food, the control unit 320 may receive information on the type or size of food via an input unit 340 disposed at the refrigerator 300 and determine the state of food in additional consideration of the input information.

As illustrated in FIG. 10A, two or more gas sensor modules 100 may be respectively mounted in different storage containers 305 in the refrigerator 300. Here, when one of the gas sensor modules 100 mounted in each of the storage containers 305 senses a concentration of a volatile organic acid and the other one senses a concentration of ammonia, kimchi and meat may be respectively stored in corresponding storage containers 305 and states thereof may be determined independently.

Otherwise, the two or more gas sensor modules 100 may be mounted in one storage container 305 and each gas sensor module 100 may be implemented to sense a different target gas from each other, such that one of the two or more gas sensor modules 100 may be selectively turned on in accordance with a type of food stored in the storage container 305.

The state of food determined by the control unit 320 may be displayed on the display unit 330 provided at the refrigerator 300. For example, when the target food is kimchi, the control unit 320 may determine a state of the kimchi as one of fresh, under-fermented, fermented, over-fermented stages in accordance with the output signal of the gas sensor module 100, and display the determined result on the display unit 330 such that the user may recognize a current state of the kimchi.

Otherwise, when the target food is meat, the control unit 320 may determine a state of meat as one of mature or spoiled stages in accordance with the output signal of the gas sensor module 100, or furthermore determine when the meat is best to be eaten. Also, the control unit 320 displays the determined result on the display unit 330.

As mentioned above, since the gas sensor module 100 may have reversibility, the gas sensor module 100 may be continuously used in the refrigerator 300 until a replacement period is reached.

Meanwhile, the refrigerator 300 may not only display the state of the target food, but may also actively manage the state of the food by controlling a temperature of the storage compartment 303.

Figure 11:
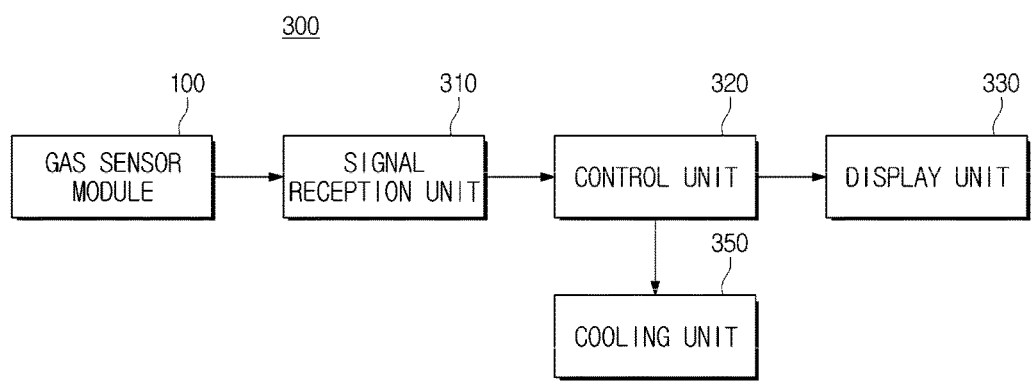
FIG. 11 is a control block diagram of a refrigerator capable of temperature control, in the refrigerator according to an embodiment of the present disclosure.

FIG. 11 is a control block diagram of a refrigerator capable of temperature control, in the refrigerator according to an embodiment of the present disclosure.

Referring to FIG. 11, the refrigerator 300 may further include a cooling unit 350 to supply cool air inside the storage compartment 303.

Since the control unit 320 may determine the state of food based on the output signal of the gas sensor module 100 and control the temperature of the storage compartment 303 in accordance with the determined result, the control unit 320 transmits a control signal to the cooling unit 350 for temperature control.

The control unit 320 may determine a proper temperature of the storage compartment 303 corresponding to the current state of food by itself in accordance with a prestored database. For example, when the target food is meat and when the current state of the meat is in the mature stage instead of the spoiled stage, the control unit 320 may determine a temperature of the storage compartment 303 that allows the meat to reach an optimal mature state or remain in the state, and transmit a control signal corresponding to the temperature to the cooling unit 350.

The control unit 320 may also receive a command related to a desired state of target food from the user via the input unit 340, and control the temperature of the storage compartment 303 in accordance with the command. Specifically, before the gas sensor module 100 detects the state of the target food or after the gas sensor module 100 determines the state of the target food, the input unit 340 may receive the command related to the desired state of the target food from the user. Here, the desired state of the target food may be the degree of maturity, the degree of freshness, and a maturing time, etc. Also, the control unit 320 may determine the current state of the target food based on the output signal of the gas sensor module 100 and display the current state on the display unit 330. Here, the current state of the target food may be a current mature state, degree of freshness, and predicted maturing time, etc. Also, the control unit 320 may determine a desired temperature and a desired oxygen exposure amount based on the desired state of the target food input in the input unit 340 and the determined state of the target food, and transmit the control signal to the cooling unit 350, etc. to control the temperature inside the storage compartment 303 and control the amount of oxygen, such that the target food may reach the desired temperature and may be exposed to the desired oxygen amount. Also, the control unit 320 may control the temperature and the amount of oxygen of the particular storage compartment 303 or the particular storage container 305 in which the gas sensor module 100 is provided to independently control them such that the target food therein reaches the desired temperature and may be exposed to the desired oxygen amount.

For example, when the target food is kimchi and the user inputs a command for a state of kimchi to remain in a fermented state in the input unit 340, the control unit 320 may determine the temperature of the storage compartment 303 that may maintain the state of kimchi in the fermented state by considering the current state of the kimchi, and transmit the control signal corresponding to the temperature to the cooling unit 350.

Specifically, when the target food is kimchi, the gas sensor module 100 may detect an organic acid and determine the state of the kimchi. That is, the control unit 320 may recognize characteristics of the target food based on the output signal detected by the gas sensor module 100 or load the characteristics of the target food from the prestored database in order to determine the current degree of maturity and the predicted maturing time of the kimchi. When it is determined that the current degree of maturity of the kimchi is an under-fermented state and the predicted maturing time is 2 weeks, the control unit 320 may control these to be displayed on the display unit 330. Also, the user may input the desired state via the input unit 340 to control the refrigerator 300. That is, the user may input the desired maturing time as 3 days via the input unit 340, and the control unit 320 may raise the temperature of the particular storage container 305 in which kimchi is stored based on the input desired maturing time and the predicted maturing time and increase the concentration of oxygen to control the maturing time to be shortened.

In addition, when the target food is meat, the gas sensor module 100 may detect ammonia to determine the state of the meat. That is, the control unit 320 may recognize characteristics of the target food based on the output signal detected by the gas sensor module 100 or load the characteristics of the target food from the prestored database in order to determine a current degree of freshness and a freshness maintenance time of the meat. When it is determined that the current degree of freshness of the meat is in a fresh state and the predicted freshness maintenance time is 3 days, the control unit 320 may control these to be displayed on the display unit 330. Also, the user may input the desired state via the input unit 340 to control the refrigerator 300. That is, the user may input the desired freshness maintenance time as 7 days via the input unit 340, and the control unit 320 may drop the temperature of the particular storage container in which meat is stored based on the input desired freshness maintenance time and the predicted freshness maintenance time and decrease the concentration of oxygen to control the maturing time to be shortened. For example, the control unit 320 may drop the temperature of the particular storage container 305 to 1 degree below zero.

Figure 12:
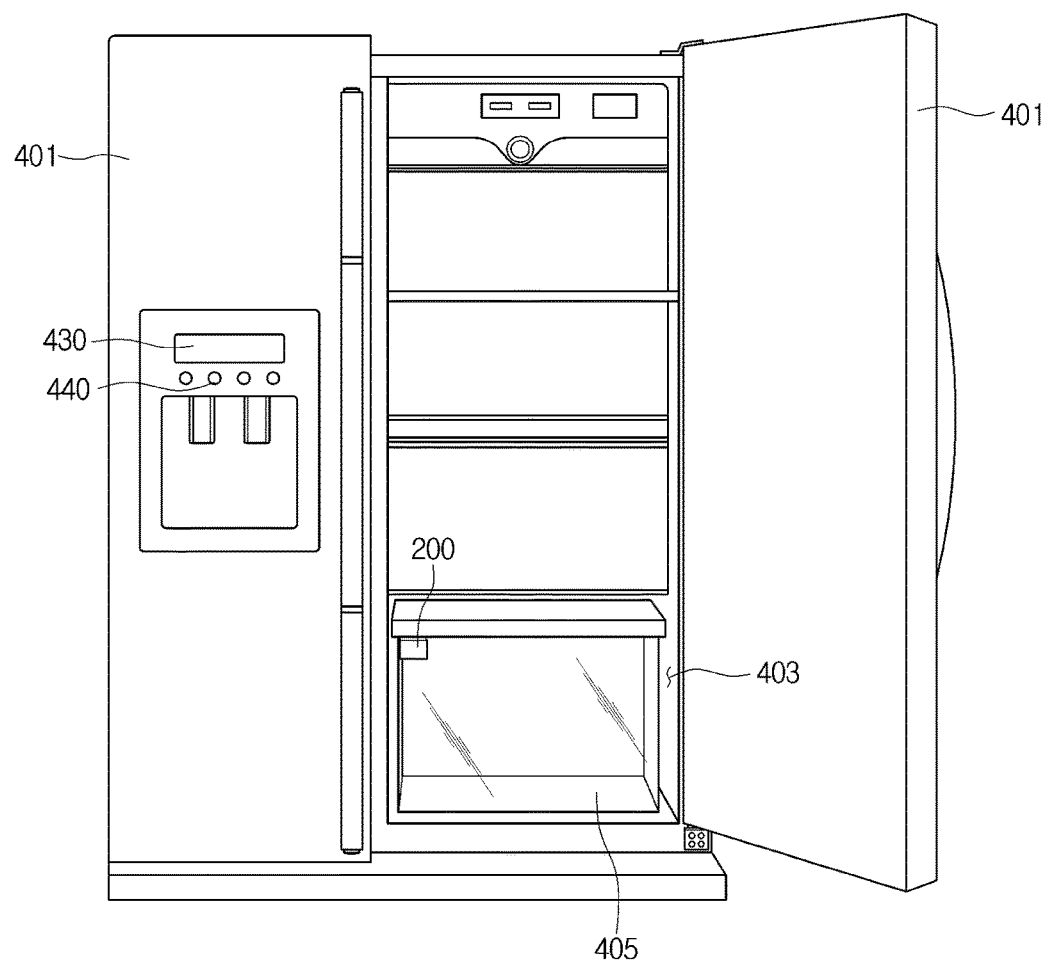
FIG. 12 illustrates an exterior view of an electronic product according to another embodiment of the present disclosure.

FIG. 12 illustrates an exterior view of an electronic product according to another embodiment of the present disclosure. An electronic product 400 according to another embodiment of the present disclosure includes the gas sensor module 200 according to another embodiment of the present disclosure. As one example of the electronic product 400, a refrigerator may be applied and both stand type and cover type may be applied as in the above-mentioned embodiment, but the refrigerator 400 having a stand type structure is illustrated in FIG. 12 for convenience.

As mentioned above, the pH change of the aqueous solution 210 in accordance with dissolution of the target gas is shown with a color change of the pH indicator in the gas sensor module 200. Since the pH change of the aqueous solution 210 is proportional to the concentration of the target gas, the concentration of the target gas may be determined by the color change of the pH indicator. Consequently, when the gas sensor module 200 is mounted at a front surface of an inner wall of a transparent storage container 405 disposed in a storage compartment 403, the user may recognize the state of the food stored in the storage container 405 by the color change of the gas sensor module 200 that is visible when a door 401 is opened.

Figure 14A:
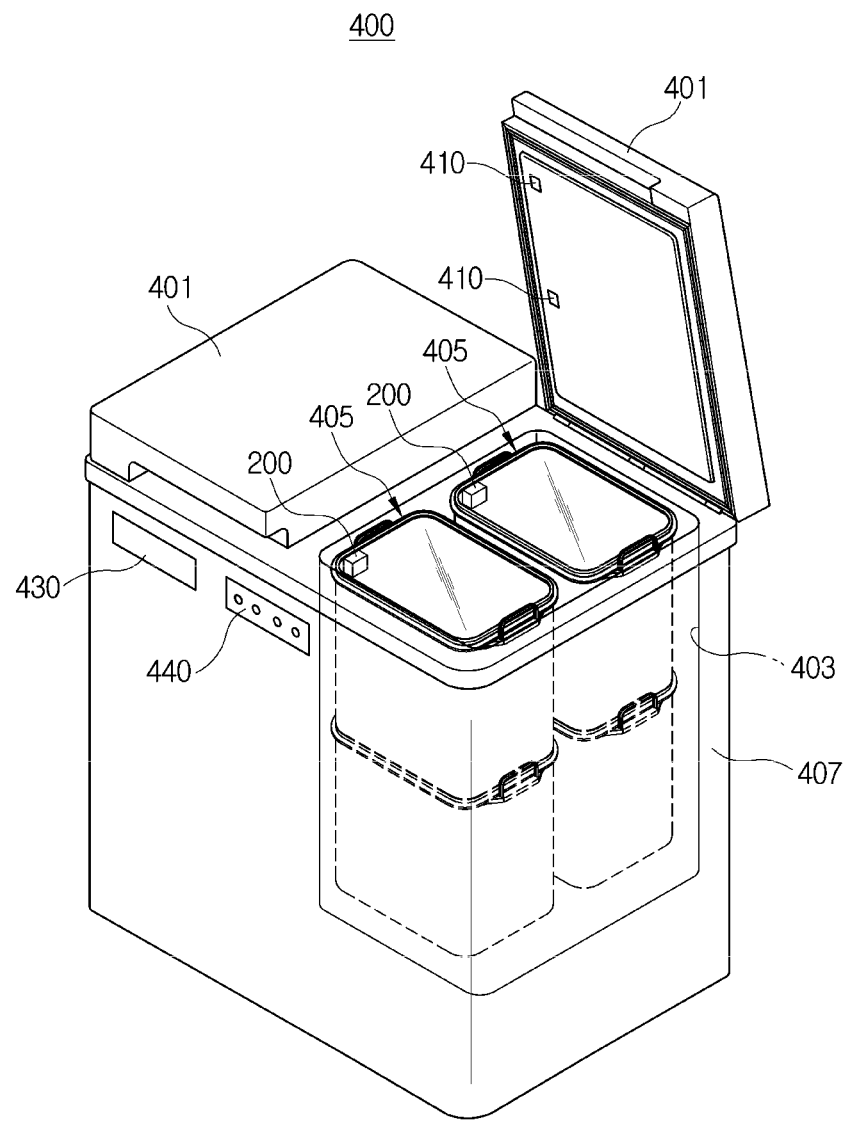
FIGS. 14A and 14B are exterior views of an electronic product that automatically detects a color change, in an electronic product according to another embodiment of the present disclosure.

As illustrated in FIG. 14A to be described below, when the refrigerator 400 has a cover type structure, a cover of the storage container 405 may be transparent to enable the color of the gas sensor module 200 mounted in the storage container 405 to be visible even without taking out the storage container 405 or opening the cover of the storage container 405, such that the user may immediately recognize the state of the food.

Meanwhile, in addition to enabling the user to directly check the color change of the gas sensor module 200, the refrigerator 400 may also automatically detect the color change of the gas sensor module 200 to determine the state of the food.

Figure 13:
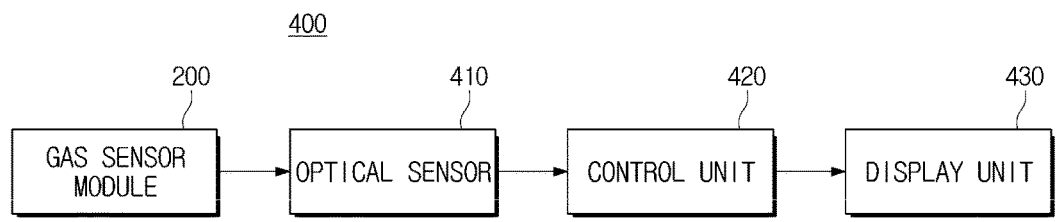
FIG. 13 is a control block diagram of an electronic product that automatically detects a color change, in an electronic product according to another embodiment of the present disclosure.
Figure 14B:
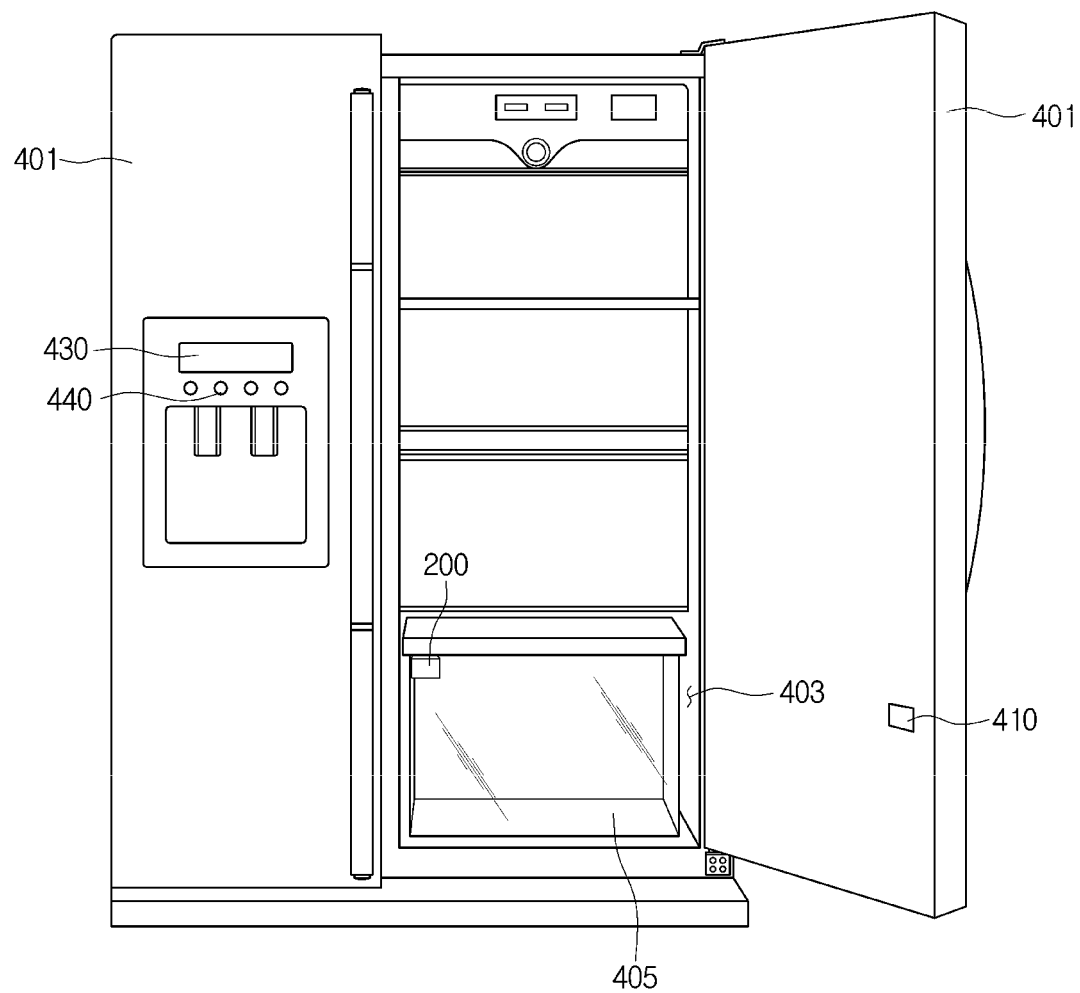

FIG. 13 is a control block diagram of an electronic product that automatically detects a color change, in the electronic product according to another embodiment of the present disclosure, and FIGS. 14A and 14B are exterior views of the electronic product that automatically detects a color change, in the electronic product according to another embodiment of the present disclosure. In the example of FIGS. 14A and 14B, the electronic product 400 is a refrigerator.

Referring to FIG. 13, the electronic product 400 includes the gas sensor module 200, an optical sensor 410 to detect a color of the gas sensor module 200, a control unit 420 to determine a state of target food based on the color of the gas sensor module 200 detected by the optical sensor 410, and a display unit 430 to display the determined state of the target food.

Referring to FIGS. 14A and 14B, the optical sensor 410 is mounted on a back surface of the door 401, i.e. a surface facing the gas sensor module 200 when the door 401 is closed. The gas sensor module 200 mounted inside the storage container 405 is visible from the outside through the transparent cover or a transparent body of the storage container 405, and when the door 401 is closed, the optical sensor 410 detects the color of the gas sensor module 200 and transmits an output signal to the control unit 420.

The control unit 420 may determine the state of food stored in the storage container 405 based on the output signal of the optical sensor 410, and display the result on the display unit 430. Also, when information on the target food is input from the user via an input unit 440, the control unit 420 may consider the information in determining the state of the target food.

According to the refrigerator 400 in accordance with this embodiment, the user may determine the state of food by opening the door 401 to directly check the color of the gas sensor module 200, and may also check the state of food determined by the refrigerator 400 itself using the optical sensor 410 by looking at the information displayed on the display unit 430.

Meanwhile, similar to the refrigerator 300 in accordance with the above-mentioned embodiment, the refrigerator 400 in accordance with this embodiment may also not only display the state of the target food but also may actively control the temperature of the storage compartment 403 based on the current state of the target food. The content related to temperature control is the same as that described in the above-mentioned embodiment related to the refrigerator 300.

In addition, since the refrigerator 400 may further include the gas sensor module 100 to sense the pH change of the aqueous solution by the electrochemical method and the signal reception unit to receive the signal of the gas sensor module 100, the two gas sensor modules 100 and 200 may be mounted in one storage container 405. In this case, the user may determine the state of the target food by directly checking the color change of the gas sensor module 200, visually, and may also check the state of the target food determined by the refrigerator 400 based on the output signal of the gas sensor module 100 through the display unit 430.

Hereinafter, an embodiment of a gas sensor assembly including a gas sensor module will be described with reference to FIGS. 15A and 15B.

Figure 15A:
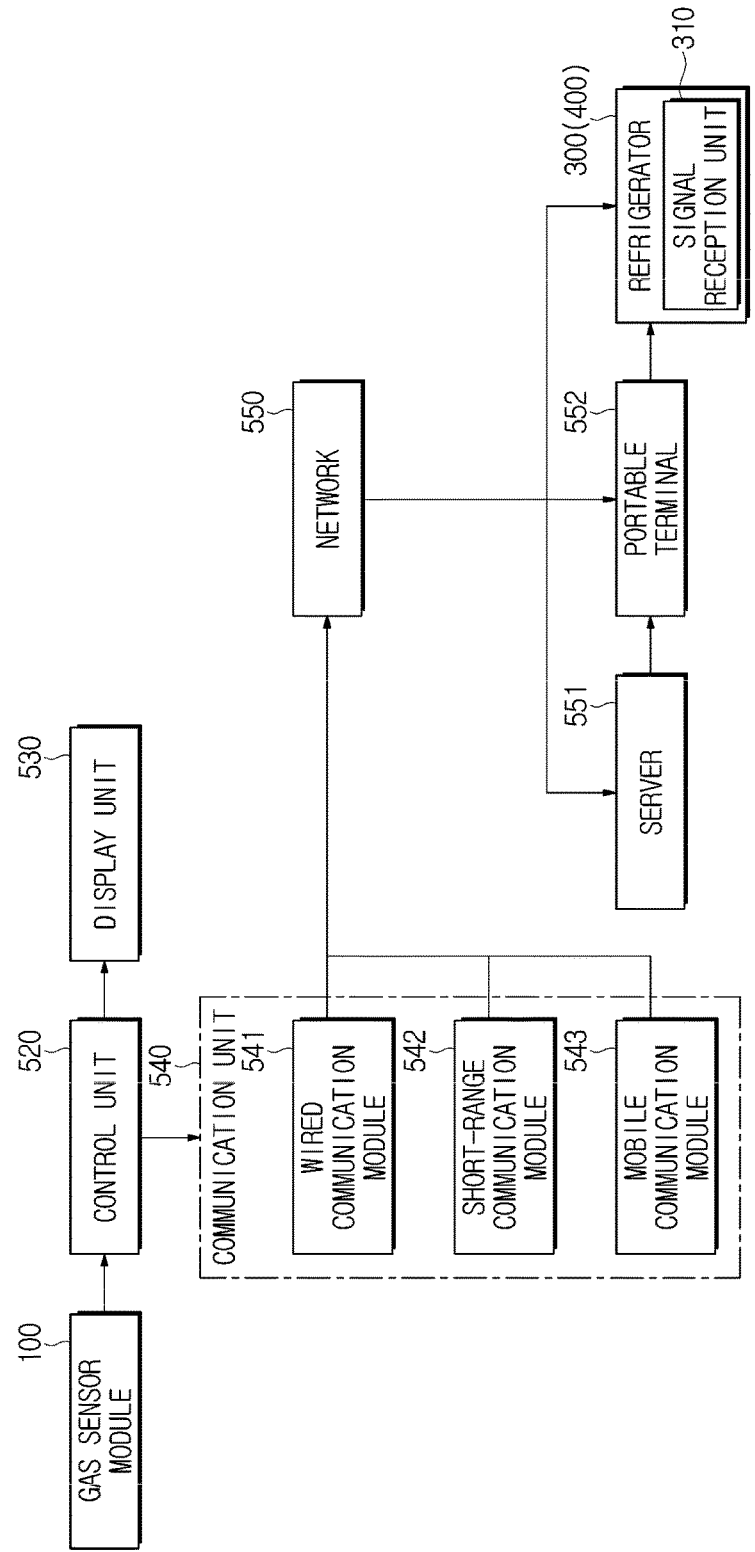
FIG. 15A is a block diagram of a gas sensor assembly according to an embodiment.

FIG. 15A is a block diagram of a gas sensor assembly according to an embodiment.

The gas sensor assembly 500 detects and determines a state of target food in the storage compartment or the storage containers by being attached to the storage compartment or the storage containers of a refrigerator, and then communicates the determined state to the refrigerator 300 or 400. Also, the gas sensor assembly 500 may be provided in a structure capable of being attached to or detached from the storage compartment or the storage containers.

Specifically, the gas sensor assembly 500 may include the gas sensor module 100, a display unit 530, a control unit 520, and the communication unit 540.

The gas sensor module 100 may be the same as or different from the gas sensor module of FIGS. 1 to 14B. Also, the display unit 530 may be the same as or different from the display unit of FIGS. 9 to 14B.

The control unit 520 may determine the current state of the target food by receiving the output signal detected by the gas sensor module 100, and may transmit the control signal to the display unit 530 to display the determined state of the target food on the display unit 530. The detailed function of the control unit 520 that determines the state of the target food and enables the determined state to be displayed on the display unit 530 may be the same as or different from the control unit of FIGS. 9 to 14B.

In addition, the control unit 520 may communicate the determined state of the target food and the output signal received from the gas sensor module 100 to the communication unit 540 in order to control the determined state and the output signal to be transmitted to another apparatus including the refrigerator 300 or 400.

In addition, the control unit 520 may function as a central processing unit, a type of the central processing unit may be a microprocessor, and the microprocessor is a processing unit in which an arithmetic and logic unit, a register, a program counter, a command decoder, or a control circuit is provided on at least one silicon chip.

In addition, the microprocessor may include a graphic processing unit (GPU) for graphic processing of images or videos. The microprocessor may be implemented in a system-on-chip (SoC) form including a core and the GPU. The microprocessor may include a single core, a dual core, a triple core, a quad core, and cores of multiples thereof.

In addition, the control unit 520 may include a graphic processing board including the GPU, a random access memory (RAM), or a read-only memory (ROM) on a separate circuit board electrically connected to the microprocessor.

The communication unit 540 may be connected to a network 550 by wire or wirelessly to communicate with another external electronic device or a server 551. The communication unit 540 may exchange data with the server 551 connected via a home server or other electronic devices within a household. Also, the communication unit 540 may perform data communication in accordance with a standard of the home server.

The communication unit 540 may transmit and receive data related to remote controlling via the network 550, and may transmit and receive data on the operation, etc. of the refrigerator 300 or 400. Furthermore, the communication unit 540 may receive information on a lifestyle of the user and data related to characteristics of the target food from the server 551 to utilize the information and the data in the operation of the refrigerator 300 or 400. Furthermore, the communication unit 540 may not only perform data communication with the server 551, but also with a portable terminal 552 of the user.

The communication unit 540 may be connected to the network 550 by wire or wirelessly and exchange data with the server 551, the portable terminal 552, or the refrigerator 300 or 400. The communication unit 540 may include one or more elements communicating with the external refrigerator 300 or 400. For example, the communication unit 540 may include a short-range communication module 542, a wired communication module 541, and a mobile communication module 543.

The short-range communication module 542 may be a module for a short-range communication within a predetermined distance. The short-range communication technology may include a wireless LAN, W-Fi, Bluetooth, Zigbee, Wi-Fi direct (WFD), ultra wideband (UWB), infrared data association (IrDA), Bluetooth low energy (BLE), near field communication (NFC), etc. but is not limited thereto.

The wire communication module 541 refers to a module for a communication using an electrical signal or an optical signal. The wire communication technology may include a pair cable, a coaxial cable, an optical fiber cable, an Ethernet cable, etc. but is not limited thereto.

The mobile communication module 543 may transmit and receive a wireless signal with at least one of a base station, an external terminal, and the server 551 in a mobile communication network. The wireless signal may include a voice call signal, a video call signal, or various forms of data in accordance with transmission and reception of text/multimedia messages.

Consequently, the communication unit 540 may communicate the determined state of the target food or the output signal of the gas sensor module to the signal reception unit 310 of the refrigerator 300 or 400, and the refrigerator 300 or 400 may recognize the states of a plurality of storage compartments and storage containers, and control temperatures thereof.

Figure 15B:
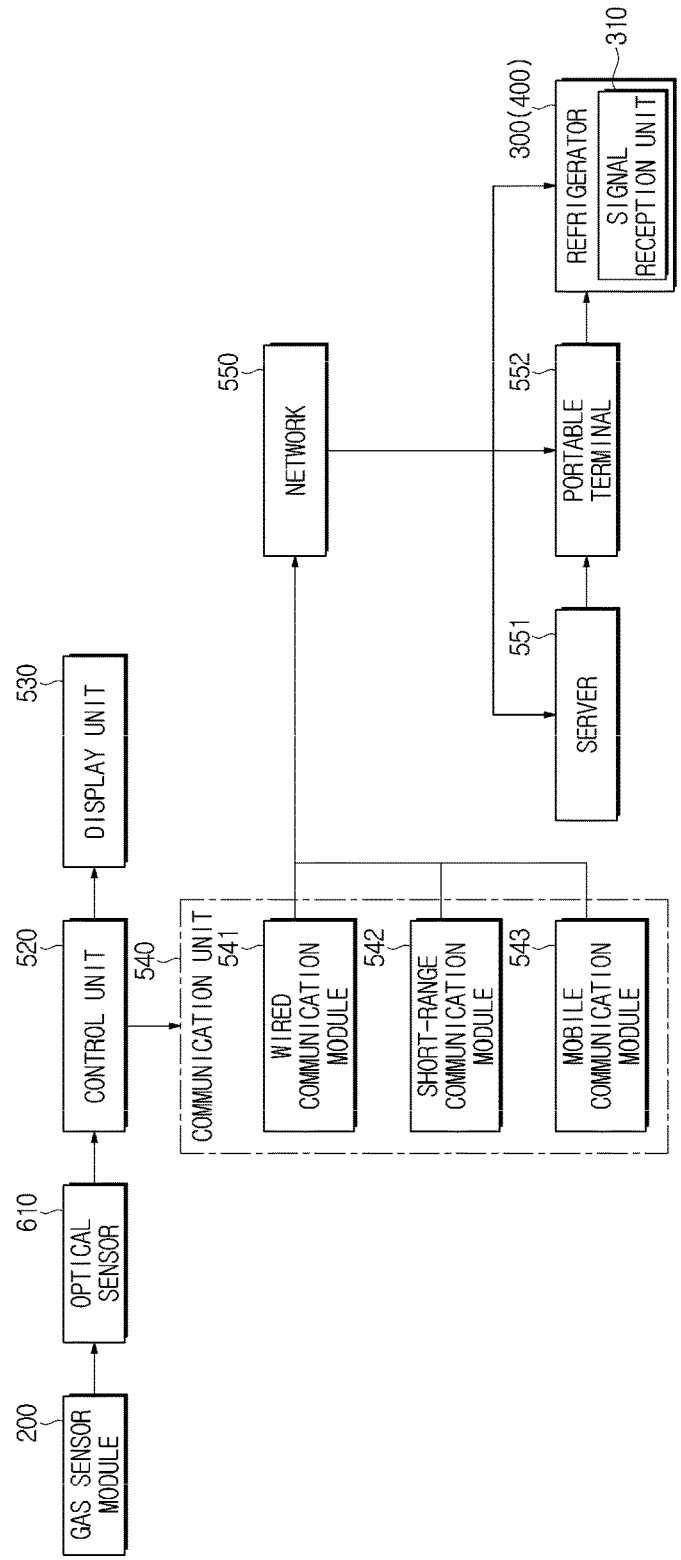
FIG. 15B is a block diagram of a gas sensor assembly according to another embodiment.

FIG. 15B is a block diagram of a gas sensor assembly according to another embodiment.

The gas sensor assembly 500 detects and determines a state of target food in the storage compartment or the storage container by being attached to the storage compartment or the storage container of the refrigerator, and then communicates the determined state to the refrigerator 300 or 400. Also, the gas sensor assembly 500 may be provided in a structure capable of being attached to or detached from the storage compartment or the storage container.

Specifically, the gas sensor assembly 500 may include the gas sensor module 200, an optical sensor 610, the display unit 530, the control unit 520, and the communication unit 540.

The gas sensor module 200 may be the same as or different from the gas sensor module 200 of FIGS. 12 to 14B. Also, the display unit 530, the control unit 520, and the communication unit 540 may be the same as or different from the display unit 530, the control unit 520, and the communication unit 540 of FIG. 15A.

The optical sensor 610 may be the same as or different from the optical sensor 410 of FIGS. 13 to 14B.

Figure 16A:
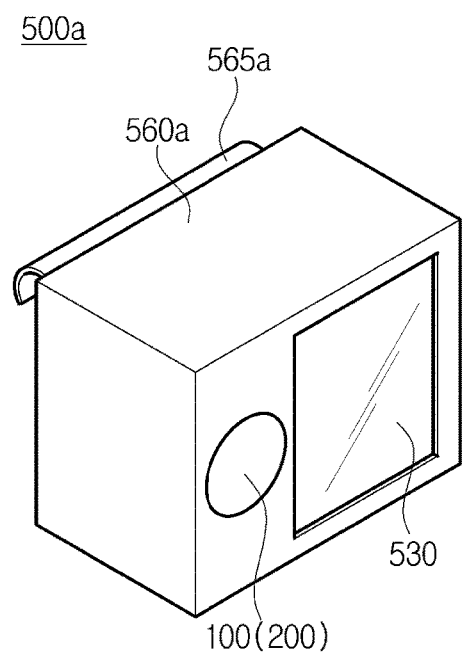
FIGS. 16A and 16B are perspective views of a gas sensor assembly according to an embodiment.
Figure 16B:
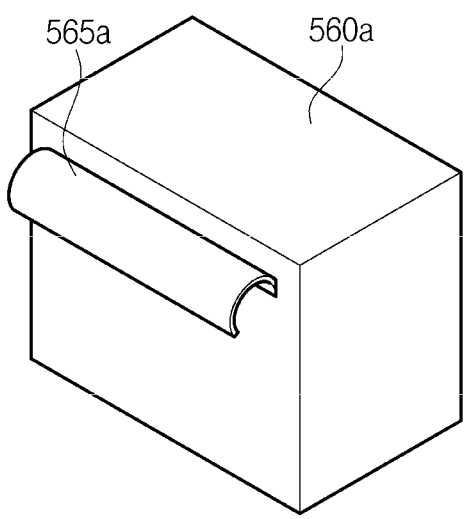

FIGS. 16A and 16B are perspective views of a gas sensor assembly according to an embodiment.

A gas sensor assembly 500a may include the gas sensor module 100 or 200, the display unit 530, and a housing 560a for a gas sensor assembly.

The gas sensor module 100 or 200 is provided at a front surface of the gas sensor assembly 500a. Also, the gas sensor module 100 or 200 may be the same as or different from the gas sensor module 100 or 200 of FIGS. 1 to 14B.

The display unit 530 may be provided at the front surface of the gas sensor assembly 500a to display the detected state of the target food or the desired state of the target food. Also, a light emitting diode (LED) technology, a liquid crystal display (LCD) technology, or a light emitting polymer display (LPD) technology may be used in the display unit 530. Various display technologies other than the above may also be used as an example of a technology used in the display unit 530. Also, the display unit 530 may the same as or different from the display unit of FIGS. 9 to 14B.

The housing 560a for a gas sensor assembly protects and supports inner configurations of the gas sensor assembly 500a.

Specifically, the housing 560a for a gas sensor assembly may surround all surfaces of the gas sensor assembly 500a and form an outer wall. Also, a hole through which the gas sensor module 100 or 200 and the display unit 530 are exposed to the outside may be formed at a front surface thereof. Also, a detachment member 565a may be provided at a rear surface thereof.

The detachment member 565a may be formed at the rear surface of the housing 560a for a gas sensor assembly to have a curved surface and may be coupled to a column 570a for detachment provided at one side surface of a storage container 505. Due to this, the gas sensor assembly 500a may be easily detached from the storage container 505.

Figure 17A:
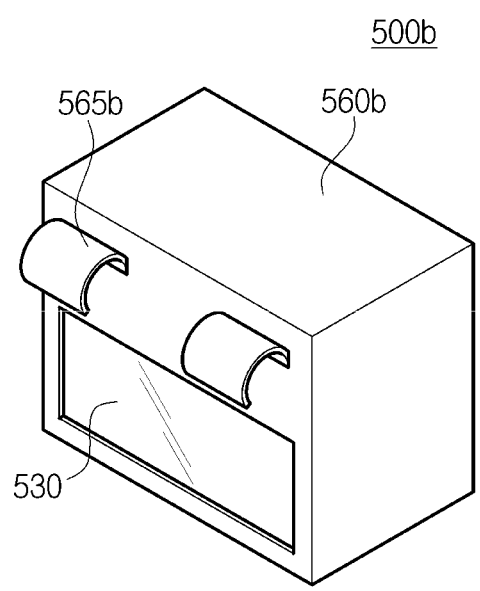
FIGS. 17A and 17B are perspective views of a gas sensor assembly according to another embodiment.
Figure 17B:
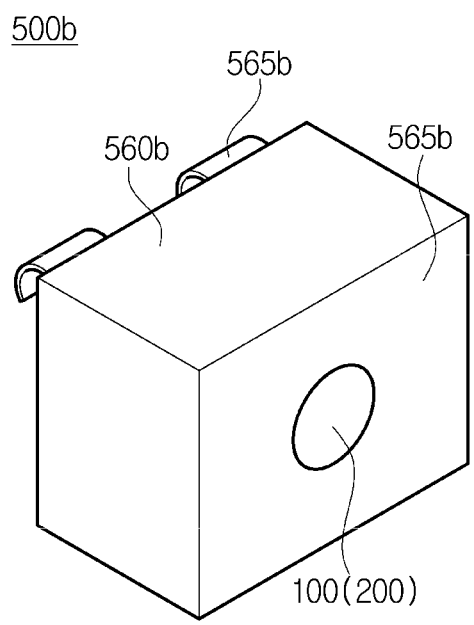

FIGS. 17A and 17B are perspective views of a gas sensor assembly according to another embodiment.

A gas sensor assembly 500b may include the gas sensor module 100 or 200, the display unit 530, and a housing 560b for a gas sensor assembly.

The gas sensor module 100 or 200 is provided at a front surface of the gas sensor assembly 500b. Also, the gas sensor module 100 or 200 may be the same as or different from the gas sensor module 100 or 200 of FIGS. 1 to 14B.

The display unit 530 may be provided at the front surface of the gas sensor assembly 500b to display the detected state of the target food or the desired state of the target food. Also, the LED technology, the LCD technology, or the LPD technology may be used in the display unit 530. Various display technologies other than the above may also be used as an example of a technology used in the display unit 530. Also, the display unit 530 may the same as or different from the display unit of FIGS. 9 to 14B.

The housing 560b for a gas sensor assembly protects and supports inner configurations of the gas sensor assembly 500b.

Specifically, the housing 560b for a gas sensor assembly may surround all surfaces of the gas sensor assembly 500b and form an outer wall. Also, a hole through which the display unit 530 is exposed to the outside may be formed at a front surface thereof, and a detachment member 565b may be provided. Also, a hole through which the gas sensor module 100 or 200 is exposed to the outside may be formed at a rear surface thereof.

The detachment member 565b may be formed at the front surface of the housing 560b for a gas sensor assembly to have a curved surface and may be coupled to a column 570b for detachment provided at one side surface of the storage container 505. Due to this, the gas sensor assembly 500b may be easily detached from the storage container 505.

Figure 18A:
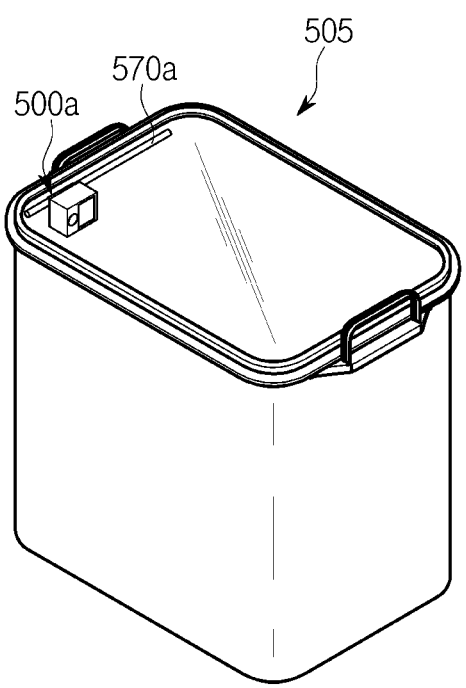
FIG. 18A is a perspective view of a gas sensor assembly attached to a storage container according to an embodiment.

FIG. 18A is a perspective view of a gas sensor assembly attached to a storage container according to an embodiment.

As illustrated in FIG. 18A, the column 570a for detachment having a cylindrical shape is provided at one side surface of the storage container 505, and the detachment member 565a provided at the rear surface of the gas sensor assembly 500a is connected to the column 570a for detachment. Consequently, the gas sensor assembly 500a may be fixed to the one side surface of the storage container 505. In this case, the gas sensor module 100 or 200 provided at the front surface of the gas sensor assembly 500a may determine the state of target food in the storage container 505, and display the determined state on the display unit 530 provided at the front surface of the gas sensor assembly 500a, such that the user may recognize the current state of the target food.

Figure 18B:
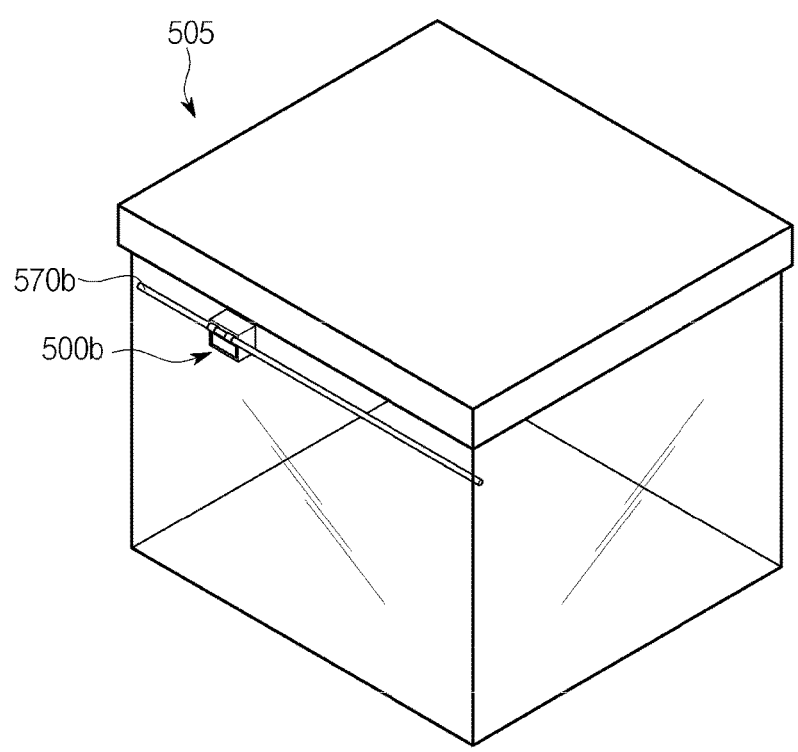
FIG. 18B is a perspective view of a gas sensor assembly attached to a storage container according to another embodiment.

FIG. 18B is a perspective view of a gas sensor assembly attached to a storage container according to another embodiment.

Referring to FIG. 18B, the column 570b for detachment having a cylindrical shape is provided at one side surface of the storage container 505, and the detachment member 565b provided at the rear surface of the gas sensor assembly 500b is connected to the column 570b for detachment. Consequently, the gas sensor assembly 500b may be fixed to the one side surface of the storage container 505. In this case, the gas sensor module 100 or 200 provided at the front surface of the gas sensor assembly 500b may determine the state of target food in the storage container 505, and display the determined state on the display unit 530 provided at the front surface of the gas sensor assembly 500b, such that the user may recognize the current state of the target food. Hereinafter, an embodiment related to a control method for an electronic product according to one aspect of the present disclosure will be described.

Figure 19:
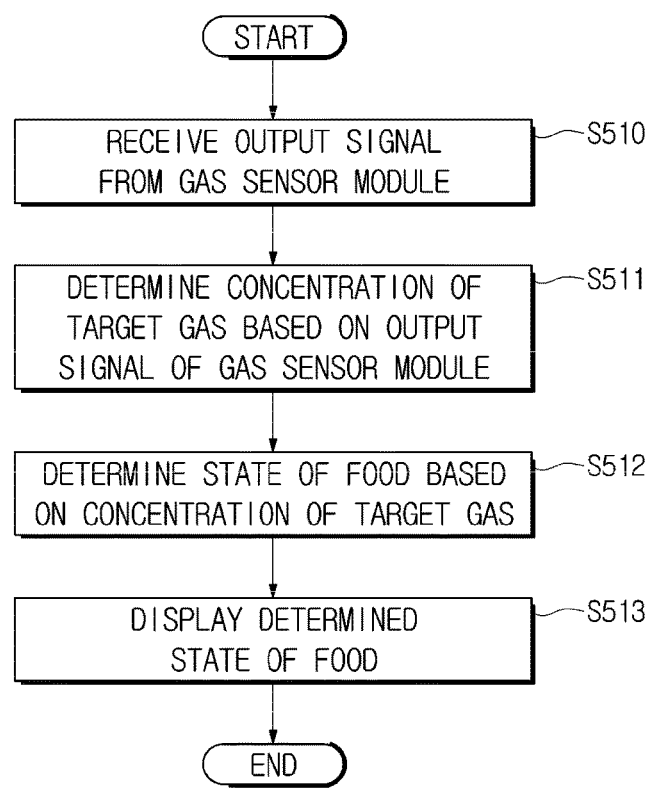
FIG. 19 is a flow chart related to a control method for an electronic product according to an embodiment of the present disclosure.

FIG. 19 is a flow chart related to a control method for an electronic product according to an embodiment of the present disclosure. The electronic product 300 in accordance with the embodiment of FIGS. 9, 10A, and 10B may be applied in the control method for the electronic product according to this embodiment, and the electronic product 300 is a refrigerator.

Referring to FIGS. 19, an output signal is received from a gas sensor module (S510). When a target gas is dissolved in the aqueous solution 110 of the gas sensor module 100 and a pH change is caused, the pH change causes the potential difference between the two electrodes 120 and 130, and the gas sensor module 100 senses the potential difference to transmit the output signal to the signal reception unit 310 of the refrigerator 300.

The concentration of the target gas is determined based on the output signal of the gas sensor module (S511). Since the output signal of the gas sensor module 100 is proportional to the concentration of the target gas, the relation between the output signal and the concentration of the target gas may be prestored and used in determining the concentration of the target gas.

The state of food is determined based on the concentration of the target gas (S512). Here, since the target gas corresponds to an index that may determine the state of the food, the concentration of the target gas varies in accordance with the state of the food. Consequently, a database including the relation between the state of the food and the concentration of the target gas may be prebuilt and used in determining the state of the food.

In addition, the determined state of the food is displayed (S513). The user may perform proper management of the food by looking at the determined state of the food.

Figure 20:
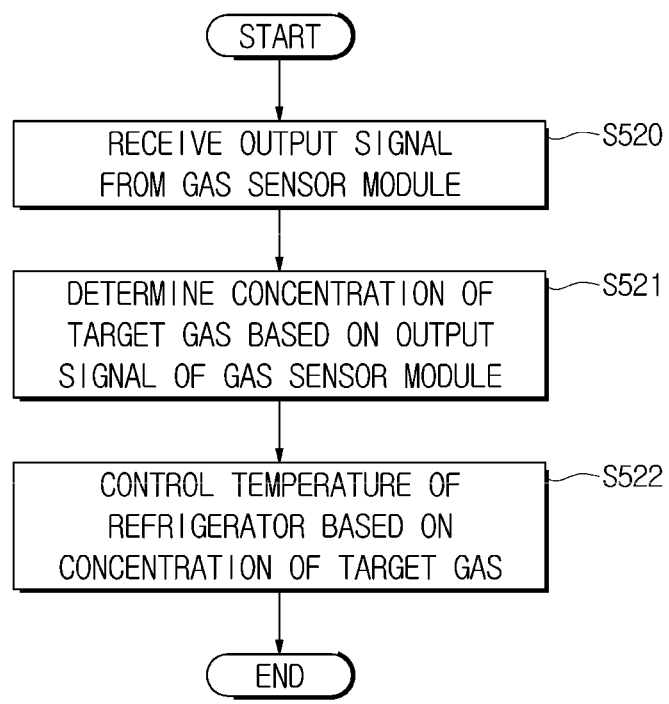
FIG. 20 is a flow chart related to a method of controlling a temperature of a refrigerator, in a control method for an electronic product according to an embodiment of the present disclosure.

FIG. 20 is a flow chart related to a method of controlling a temperature of a refrigerator, in a control method for an electronic product according to an embodiment of the present disclosure.

Referring to FIG. 20, the output signal is received from the gas sensor module (S520), and the concentration of the target gas is determined based on the output signal of the gas sensor module (S521).

In addition, the temperature of the refrigerator is controlled based on the concentration of the target gas (S522). The control unit may determine the proper temperature corresponding to the current state of food by itself in accordance with the prestored database or receive a command related to the state of food from the user and determine the temperature to reach or maintain the input state of food. The temperature control may be performed using the cooling unit disposed in the refrigerator 300.

Figure 21:
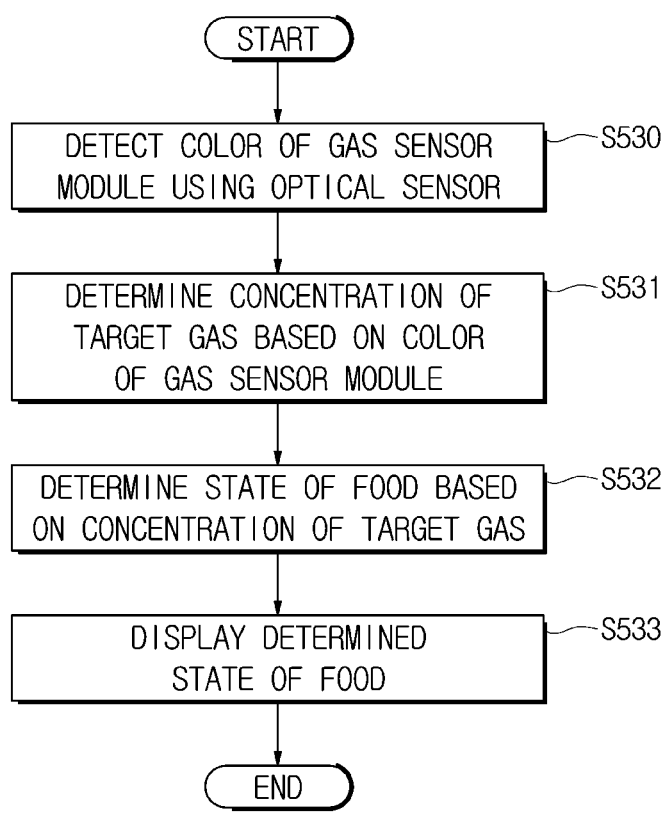
FIG. 21 is a flow chart related to a control method for an electronic product according to another embodiment of the present disclosure.

FIG. 21 is a flow chart related to a control method for an electronic product according to another embodiment of the present disclosure. Since the electronic product 400 in accordance with the embodiment of FIGS. 12 to 14A and 14B may be applied to the control method according to this embodiment, the electronic product 400 is a refrigerator.

Referring to FIG. 21, a color of the gas sensor module is detected using the optical sensor (S530). Since the pH change of the aqueous solution 210 in accordance with the dissolution of the target gas is shown with a color change of the pH indicator in the gas sensor module 200, the color of the gas sensor module 200 may be detected using the optical sensor 410 mounted on a position corresponding to the gas sensor module 200.

The concentration of the target gas is determined based on the color of the gas sensor module (S531). Since the housing 201 of the gas sensor module 200 is formed of a transparent material, the color change of the pH indicator mixed with the aqueous solution 210 is externally shown. Since the pH change of the aqueous solution 210 is proportional to the concentration of the target gas, the concentration of the target gas may be determined by the color change of the pH indicator.

The state of food is determined based on the concentration of the target gas (S532), and the determined state of the food is displayed (S533). Since description related to this is the same as the above-mentioned embodiment, it will be omitted here.

Figure 22:
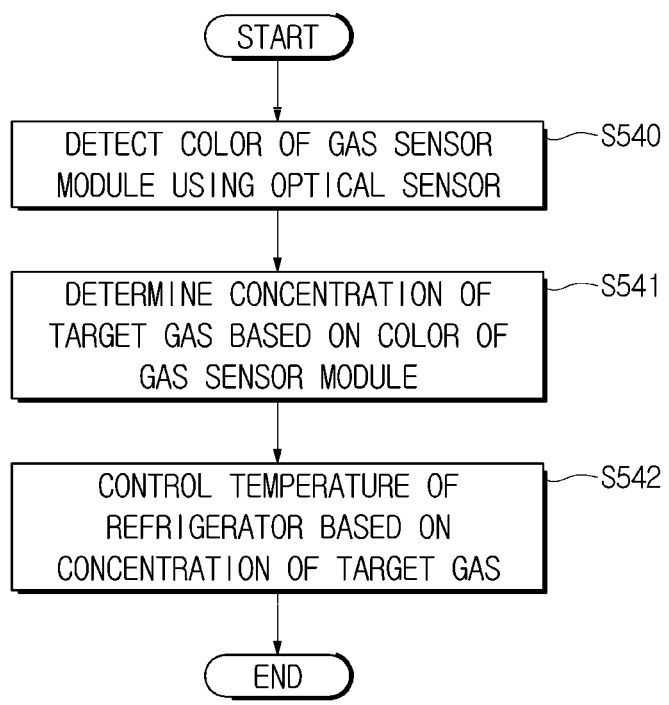
FIG. 22 is a flow chart related to a method of controlling a temperature of a refrigerator, in a control method for an electronic product according to another embodiment of the present disclosure.

FIG. 22 is a flow chart related to a method of controlling a temperature of a refrigerator, in a control method for an electronic product according to another embodiment of the present disclosure.

Referring to FIG. 22, the color of the gas sensor module is detected using the optical sensor (S540), and the concentration of the target gas is determined based on the color of the gas sensor module (S541).

In addition, the temperature of the refrigerator is controlled based on the concentration of the target gas (S542). The control unit may determine the proper temperature corresponding to the current state of food by itself in accordance with the prestored database or receive a command related to the state of food from the user and determine the temperature to reach or maintain the input state of food.

Figure 23:
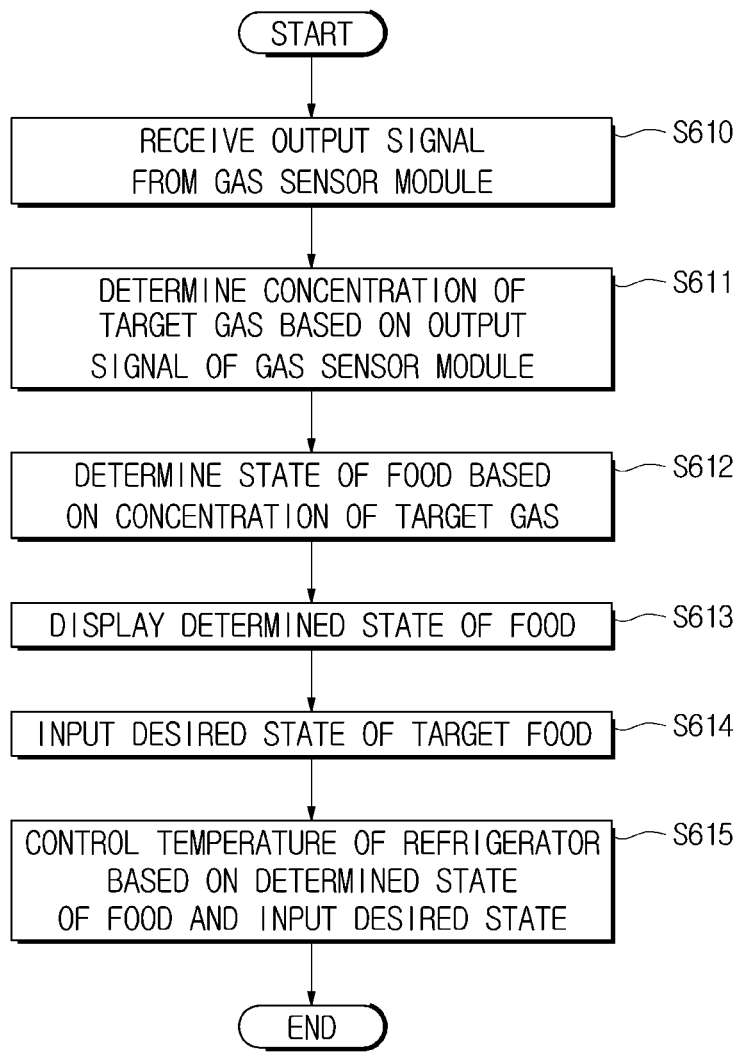
FIG. 23 is a flow chart related to an embodiment of a method of controlling a temperature of a refrigerator based on a desired state of target food input using an electrochemical sensor.

FIG. 23 is a flow chart related to an embodiment of a method of controlling a temperature of a refrigerator based on a desired state of target food input using an electrochemical sensor.

First, the gas sensor module senses an electrical capacitance of a gas using the electrochemical sensor to convert a current state of the gas within a particular area into an electrical output signal, and the signal reception unit receives the electrical output signal from the gas sensor module (S610).

Then, the signal reception unit transmits the received output signal to the control unit, and the control unit determines the concentration of the target gas within the particular area based on the output signal received from the gas sensor module (S611).

After that, the control unit determines the state of target food in the storage container based on the determined concentration of the target gas within the particular area (S612). Specifically, the control unit may determine the degree of freshness, the predicted freshness maintenance time, the degree of maturity, and the predicted maturing time of the target food. Also, the control unit transmits the control signal to the display unit such that the display unit displays the determined state of the target food (S613).

In addition, when the user inputs the desired state of the target food via the input unit (S614), the input unit converts it into an electrical input signal and transmits the signal to the control unit. Specifically, the user may input the degree of freshness, the desired freshness maintenance time, the degree of maturity, and the desired maturing time of the target food via the input unit.

Finally, the control unit controls the temperature of the refrigerator based on the determined current state of the target food and the input desired state of the target food (S615).

Figure 24:
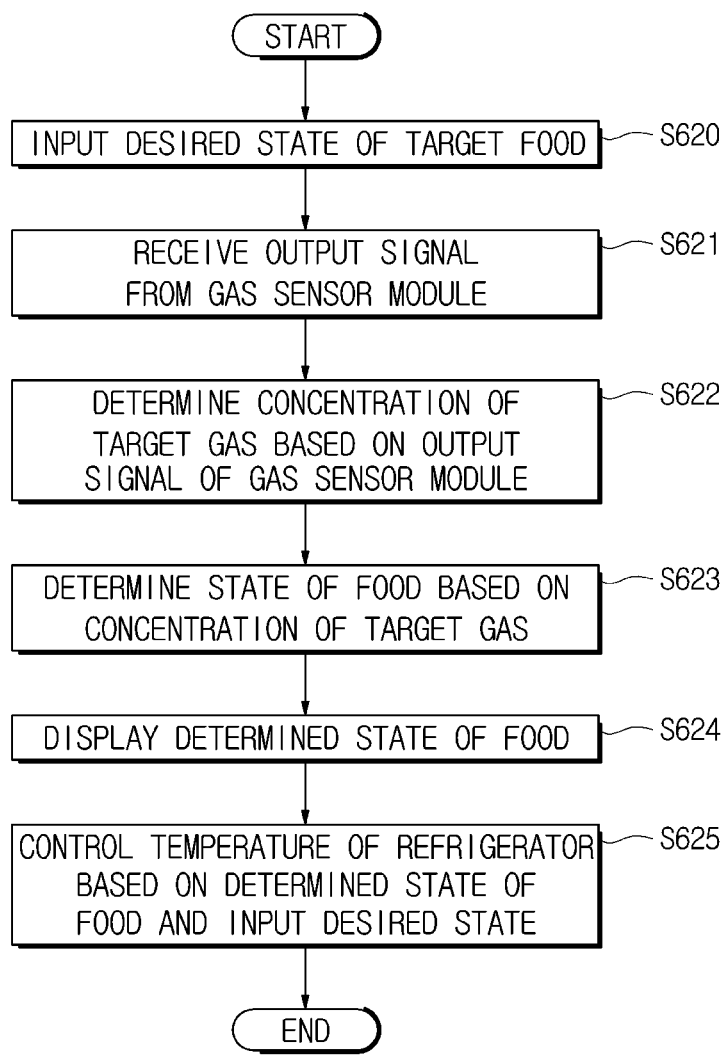
FIG. 24 is a flow chart related to another embodiment of a method of controlling a temperature of a refrigerator based on a desired state of target food input using an electrochemical sensor.

FIG. 24 is a flow chart related to another embodiment of a method of controlling a temperature of a refrigerator based on a desired state of target food input using an electrochemical sensor.

First, when the user inputs the desired state of target food via the input unit (S620), the input unit converts it into an electrical input signal and transmits the signal to the control unit. Specifically, the user may input the degree of freshness, the desired freshness maintenance time, the degree of maturity, and the desired maturing time of the target food via the input unit.

In addition, the gas sensor module senses an electrical capacitance of a gas using the electrochemical sensor to convert a current state of the gas within a particular area into an electrical output signal, and the signal reception unit receives the electrical output signal from the gas sensor module (S621).

Then, the signal reception unit transmits the received output signal to the control unit, and the control unit determines the concentration of the target gas within the particular area based on the output signal received from the gas sensor module (S622).

After that, the control unit determines the state of target food in the storage container based on the determined concentration of the target gas within the particular area (S623). Specifically, the control unit may determine the degree of freshness, the predicted freshness maintenance time, the degree of maturity, and the predicted maturing time of the target food. Also, the control unit transmits the control signal to the display unit such that the display unit displays the determined state of the target food (S624).

Finally, the control unit controls the temperature of the refrigerator based on the determined current state of the target food and the input desired state of the target food (S625).

Figure 25:
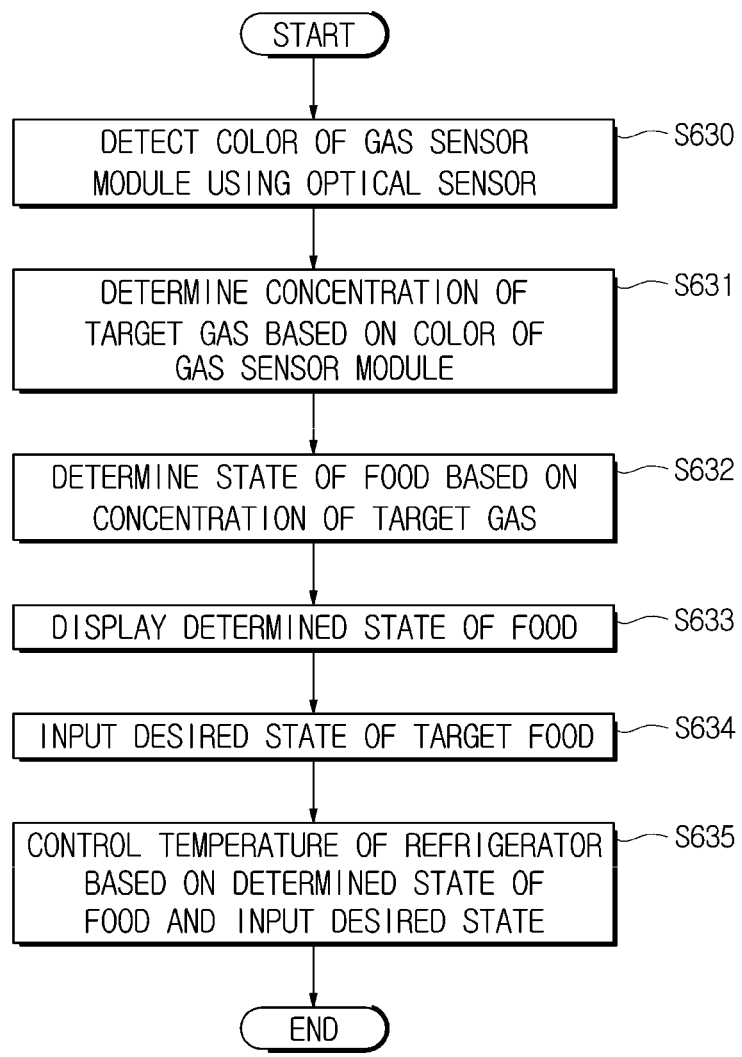
FIG. 25 is a flow chart related to an embodiment of a method of controlling a temperature of a refrigerator based on a desired state of target food input using an optical sensor.

FIG. 25 is a flow chart related to an embodiment of a method of controlling a temperature of a refrigerator based on a desired state of target food input using an optical sensor.

First, the gas sensor module detects a color of an indicator solution that is color-changed in accordance with current acidity of a gas using the optical sensor (S630).

Then, the optical sensor converts the detected color into an electrical output signal, the received output signal is transmitted to the control unit, and the control unit determines the concentration of the gas within the particular area based on the output signal received from the gas sensor module (S631).

After that, the control unit determines the state of target food in the storage container based on the determined concentration of the target gas within the particular area (S632). Specifically, the control unit may determine the degree of freshness, the predicted freshness maintenance time, the degree of maturity, and the predicted maturing time of the target food. Also, the control unit transmits the control signal to the display unit such that the display unit displays the determined state of the target food (S633).

In addition, when the user inputs the desired state of the target food via the input unit (S634), the input unit converts it into an electrical input signal and transmits the signal to the control unit. Specifically, the user may input the degree of freshness, the desired freshness maintenance time, the degree of maturity, and the desired maturing time of the target food via the input unit.

Finally, the control unit controls the temperature of the refrigerator based on the determined current state of the target food and the input desired state of the target food (S635).

Figure 26:
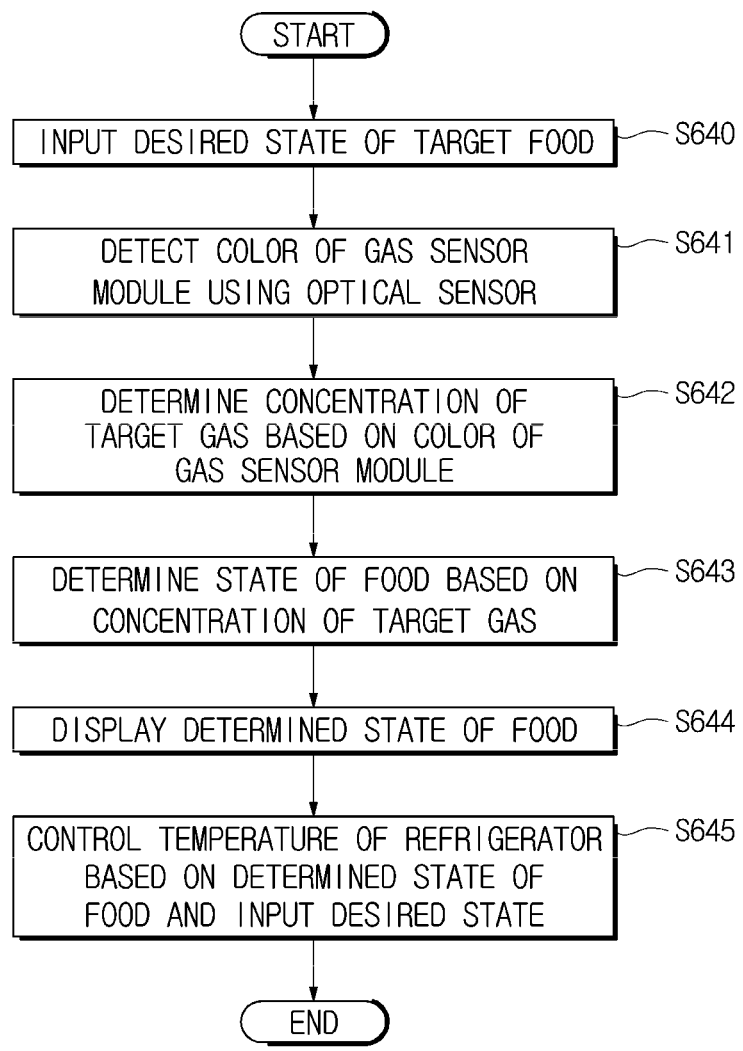
FIG. 26 is a flow chart related to another embodiment of a method of controlling a temperature of a refrigerator based on a desired state of target food input using an optical sensor.

FIG. 26 is a flow chart related to another embodiment of a method of controlling a temperature of a refrigerator based on a desired state of target food input using an optical sensor.

First, when the user inputs the desired state of the target food via the input unit (S640), the input unit converts it into an electrical input signal and transmits the signal to the control unit. Specifically, the user may input the degree of freshness, the desired freshness maintenance time, the degree of maturity, and the desired maturing time of the target food via the input unit.

In addition, the gas sensor module detects a color of an indicator solution that is color-changed in accordance with current acidity of a gas using the optical sensor (S641).

In addition, the optical sensor converts the detected color into an electrical output signal, the received output signal is transmitted to the control unit, and the control unit determines the concentration of the gas within the particular area based on the output signal received from the gas sensor module (S642).

After that, the control unit determines the state of target food in the storage container based on the determined concentration of the target gas within the particular area (S643). Specifically, the control unit may determine the degree of freshness, the predicted freshness maintenance time, the degree of maturity, and the predicted maturing time of the target food. Also, the control unit transmits the control signal to the display unit such that the display unit displays the determined state of the target food (S644).

Finally, the control unit controls the temperature of the refrigerator based on the determined current state of the target food and the input desired state of the target food (S645).

According to a gas sensor module, an electronic product having the same, and a control method for the electronic product in accordance with one aspect of the present disclosure described until now, the principle of the human olfactory organ system is employed to dissolve a target gas in an aqueous solution and sense a pH change of the aqueous solution caused by the dissolution, thereby sensing a concentration of the target gas, with superior selectivity and resolution.

In addition, by controlling the initial pH of the aqueous solution and a concentration of a conjugate acid or a conjugate base pre-dissolved in the aqueous solution, a gas sensor module having a desired sensing range and sensing resolution can be implemented.

The invention claimed is:

1. A gas sensor module configured to sense a concentration of a target gas, the gas sensor module comprising:

an aqueous solution in which ion pairs of a substance having a substantially same dissociation constant as that of the target gas are dissolved, wherein the gas sensor module is configured to sense a pH change of the aqueous solution that occurs due to the target gas being dissolved in the aqueous solution to indicate the concentration of the target gas, and wherein the aqueous solution is mixed with a pH indicator, which changes in color in accordance with the pH change of the aqueous solution.

2. The gas sensor module according to claim 1, wherein the target gas is a volatile organic acid or ammonia.

3. The gas sensor module according to claim 1, wherein a resolution of the gas sensor module varies in accordance with a concentration of the ion pairs dissolved in the aqueous solution.

4. The gas sensor module according to claim 1, wherein a sensing range of the gas sensor module with respect to the concentration of the target gas varies in accordance with an initial pH of the aqueous solution.

5. The gas sensor module according to claim 1, further comprising an electrochemical sensor configured to sense the pH change, wherein the electrochemical sensor comprises:
a working electrode, a potential of which varies in accordance with the pH change within the aqueous solution; and
a reference electrode to serve as a reference for the working electrode.

6. The gas sensor module according to claim 1, wherein the target gas is a carboxylic acid, and
the pH indicator is at least one selected from 0.001 wt% to 0.1 wt% of bromothymol blue and 0.001 wt% to 0.1 wt% of methyl red.

7. The gas sensor module according to claim 1, wherein, the target gas is ammonia, and
the pH indicator is at least one selected from 0.001 wt% to 0.1 wt% of a thymol blue reagent, 0.001 wt% to 0.1 wt% of cresol red, and 0.001 wt% to 0.1 wt% of a phenolphthalein reagent.

8. The gas sensor module according to claim 1, further comprising:
a housing configured to accommodate the aqueous solution and having an inlet into which the target gas is introduced; and
a porous membrane through which the target gas, having introduced into the inlet, permeates to dissolve into the aqueous solution.

9. An electronic product comprising the gas sensor module of claim 1.

10. The electronic product according to claim 9, wherein to indicate the concentration of the target gas, the gas sensor module generates a signal output based on the pH change, and the electronic product further comprises:
a signal reception unit configured to receive the signal output from the gas sensor module; and
a control unit configured to determine a state of target food based on the received signal output.

11. The electronic product according to claim 9, wherein the electronic product is a gas sensor assembly attachable to and detachable from at least one of a storage compartment and a storage container of a refrigerator, and further comprises:

a control unit configured to determine a state of target food based on a signal output from the gas sensor module; and
a communication unit configured to communicate the determined state of the target food to the refrigerator.

12. An electronic product comprising the gas sensor module of claim 6.

13. The electronic product according to claim 12, further comprising:
an optical sensor configured to detect a color of the gas sensor module, and
a control unit configured to determine a state of target food based on the color detected by the optical sensor.

14. The electronic product according to claim 13, further comprising the display unit configured to display the determined state of the target food.

15. A control method comprising:
using an aqueous solution, in which ion pairs of a substance having a substantially same dissociation constant as that of a target gas are dissolved, and a gas sensor module, which is configured to sense a pH change of the aqueous solution that occurs due to the target gas being dissolved in the aqueous solution and indicate the pH change by producing at least one of a signal generated based on the pH change and a color change in accordance with the pH change, to sense the pH change in response to the target gas being dissolved in the aqueous solution;
determining the concentration of the target gas based on the at least one of the signal generated based on the pH change and the color change of the gas sensor module in accordance with the pH change; and
determining a state of target food based on the determined concentration of the target gas.

16. The control method according to claim 15, further comprising displaying the determined state of the target food.

17. The control method according to claim 15, wherein:
the electronic product is a refrigerator; and
the control method for the electronic product further comprises controlling a temperature of the refrigerator based on the determined state of the target food.

18. The control method according to claim 17, wherein:
the control method further comprises receiving an input of a desired state of target food after determining the state of the target food; and
the controlling of the temperature of the refrigerator includes controlling the temperature of the refrigerator based on the determined state of the target food and the input desired state of the target food.

19. The control method according to claim 17, wherein:
the at least one of the signal and the color change is the signal;
the control method further comprises receiving an input of a desired state of target food before receiving the signal from the gas sensor module; and
the controlling of the temperature of the refrigerator includes controlling the temperature of the refrigerator based on the determined state of the target food and the input desired state of the target food.

* * * * *